(12) United States Patent
Yamaguchi et al.

(10) Patent No.: US 7,355,063 B2
(45) Date of Patent: Apr. 8, 2008

(54) SHOGAOL COMPOUND AND TYROSINASE ACTIVITY INHIBITOR COMPRISING THE COMPOUND

(75) Inventors: Shuhei Yamaguchi, Tsukuba (JP); Hisatoyo Kato, Tsukuba (JP)

(73) Assignee: Toagosei Co., Ltd., Tokyo (JP)

( * ) Notice: Subject to any disclaimer, the term of this patent is extended or adjusted under 35 U.S.C. 154(b) by 205 days.

(21) Appl. No.: 10/549,117

(22) PCT Filed: Mar. 26, 2004

(86) PCT No.: PCT/JP2004/004316

§ 371 (c)(1), (2), (4) Date: Sep. 14, 2005

(87) PCT Pub. No.: WO2004/085373

PCT Pub. Date: Oct. 7, 2004

(65) Prior Publication Data

US 2006/0173072 A1    Aug. 3, 2006

(30) Foreign Application Priority Data

Mar. 27, 2003  (JP) .............................. 2003-086818
Dec. 16, 2003  (JP) .............................. 2003-417389

(51) Int. Cl.
*C07C 69/76* (2006.01)

(52) U.S. Cl. .................. 560/55; 560/60; 568/309; 568/716; 568/763; 568/766; 514/475; 514/543

(58) Field of Classification Search ............... 514/475, 514/543; 560/55, 60; 568/309, 716, 763, 568/766

See application file for complete search history.

(56) References Cited

FOREIGN PATENT DOCUMENTS

JP      2001-131033 A    5/2001

OTHER PUBLICATIONS

T.Nakazawa, K.Ohsawa□□Metabolism of [6]-gingerol in rats□□Life Sciences 70 (2002) 2165-2175.*
T.Nakazawa, K.Ohsawa,□□Metabolism of [6]-gingerol in rats,□□Life Sciences 2002, 70, 2165-2175.*
Sang-Sup Lee,□□Re-examination of 6-shogaol biotransformation by *Aspergillus niger*□□Archives of Pharmacal Research 1995, 18(2), 136-7.*
Takahashi et al., "Biotransformation of 6-gingerol and 6-shogaol by *Aspergillus niger*", Phytochemistry, vol. 34, No. 6, 1993, pp. 1497-1500.
Lee et al., "Biotransformation of dehydroparadols by *Aspergillus niger*", Database accession No. 1996:64711.
Takahiro Nakazawa, et al., "Life Sciences", 2002, pp. 2165-2175, vol. 70, No. 18.
International Search Report dated Jul. 13, 2004.

* cited by examiner

*Primary Examiner*—Yvonne Eyler
*Assistant Examiner*—Sudhakar Katakam
(74) *Attorney, Agent, or Firm*—Sughrue Mion, PLLC

(57) ABSTRACT

The compound represented by the following formula (1):

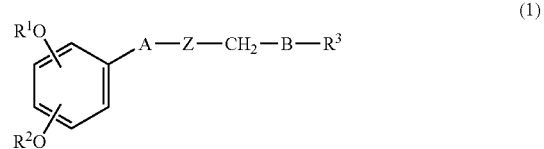

wherein A, B, R1, R2, R3 and Z are as defined in the specification is analogous to shogaol and gingerol useful in the fields of foods, medicines, quasi-drugs, cosmetics, etc., and more highly active in tyrosinase activity inhibition, etc. than shogaol and gingerol.

7 Claims, No Drawings

SHOGAOL COMPOUND AND TYROSINASE ACTIVITY INHIBITOR COMPRISING THE COMPOUND

TECHNICAL FIELD

The present invention relates to a novel compound having a chemical structure similar to shogaol and gingerol, which are useful in the fields of foods, medicines, quasi-drugs, cosmetics, etc., and to an intermediate for producing the same. In addition, it relates to a tyrosinase activity inhibitor, hyaluronic acid-degrading enzyme inhibitor, an antioxidant, or the like comprising the novel compound as an active ingredient.

BACKGROUND ART

Pigmentation due to spots, freckles, and the like emerges through formation of melanin pigment in epidermal chromocytes and abnormal deposition thereof in epidermis caused by ultraviolet exposure and the like. Melanin pigment is synthesized by metabolism of L-tyrosine as one of amino acids into L-dopa and then L-dopaquinone by the action of tyrosinase as an oxidative enzyme thereof and subsequent various pathways (cf. e.g., Fine Chemicals, issue on Mar. 15, 1999, "Special Topic: Bihakuzai no Kaihatsu to Seihin Tenkai (Development and Products of Whitening Agents)"; and Fragrance Journal, issue on September 1997, "Special Topic: Saikin no Bihakuzai no Kenkyu Kaihatsu Doko (Recent Trend of Researches and Development of Whitening Agent)"). Thus, in order to prevent pigmentation due to spots, freckles, and the like, it is important to inhibit activity of tyrosinase which plays an important role for melanin pigment synthesis.

Hitherto, for preventing and improving spots, freckles, and the like, there have been used pharmaceutical agents such as placenta extracts, vitamin C, vitamin C derivatives, kojic acid, and arbutin. However, these agents have resulted in no sufficient effect. Moreover, in Europe and the United States, hydroquinone has been used for the purpose of decoloration of dye freckles but use thereof is limited because of problems in safety. Furthermore, recently, a possibility of carcinogenicity is also pointed out for kojic acid and thus becomes a problem.

On the other hand, shogaol and gingerol are components of ginger extracts and they are known to have, for example, a blood cirdulation-facilitating effect (JP-A-6-183959), a body odor-preventing effect (U.S. Pat. No. 6,264,928), an antioxidation effect (H. Kikuzaki, N. Nakatani, "Antioxidant Effects of Some Ginger Constituents", J. Food Sci., Vol. 58, No. 6, 1407-1410 (1993)), a moisturizing effect (supervising editor: Masato Suzuki, "Atarashii Keshohin Kinousozai (Novel Cosmetic Functional materials) 300, first volume", pp. 311-312, CMC Publishing, 2002), and the like effects. Moreover, metabolic routes of shogaol and gingerol have been also researched and structures of metabolites thereof have been reported (H. Takahashi and other three authors, Phytochemistry, Vol. 34, 1497-1500 (1993) and S. S. Lee, Arch. Pharm. Res., Vol. 18, 136-137 (1995)).

The present inventors had investigated methods capable of mass production of shogaol and they developed an industrial production process of a specific shogaol as a target. Thus, they applied a patent application (Japanese Patent Application No. 2003-327574) on the specific shogaol and the process for producing the same, and simultaneously, they reported that shogaol has a property of inhibiting activity of tyrosinase. However, since the shogaol obtained by the production process is insufficient in water solubility, there is a case that it is difficult to apply to human and hence it is desired to develop a compound which is more soluble in water.

DISCLOSURE OF THE INVENTION

It is an object of the invention to provide a compound, which is the same class as shogaol and gingerol useful in the fields of foods, medicines, quasi-drugs, cosmetics, etc. and which is more highly active in the inhibition of tyrosinase activity or the like than shogaol and gingerol.

As a result of extensive studies for solving the above problems, the present inventors have found a novel compound having a basic structure the same as that of shogaol and gingerol and having properties the same as those of known shogaol and gingerol and also they have found that the compound satisfactory acts as a tyrosinase activity inhibitor or the like. Thus, they have accomplished the invention.

The invention is a compound represented by the following formula (1):

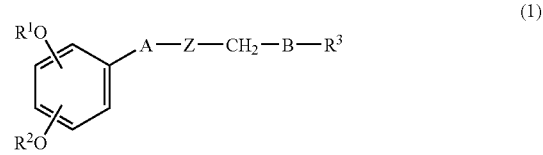

wherein $R^1$ is a hydrogen atom, a lower alkyl group, or a protective group of a phenolic hydroxyl group, $R^2$ is a hydrogen atom or a protective group of a phenolic hydroxyl group, A is an alkylene group having 1 to 4 carbon atoms, B is an alkylene group having 1 to 12 carbon atoms, $R^3$ is —COOR$^4$ (wherein $R^4$ is a protective group of a carboxyl group), a carboxyl group, or —CH$_2$OH, and Z is —CO—CH=CH—, —CHOH—CH=CH—, —CHOH-1,2-epoxy-, —CO—CH$_2$CH$_2$—, —CHOH—CH$_2$CH$_2$—, —CO—CH$_2$CHOH—, —CHOH—CH$_2$CHOH—, —CO—CH$_2$CHOR$^5$—, —CHOH—CH$_2$CHOR$^5$—, a ketal derivative of —CO—CH=CH—, or a ketal derivative of —CO—CH$_2$CH$_2$— and $R^5$ is a lower alkyl group when $R^3$ is a —COOR$^4$ group, Z is —CO—CH=CH—, —CHOH—CH=CH—, —CHOH-1,2-epoxy-, —CHOH—CH$_2$CH$_2$—, —CHOH—CH$_2$CHOH—, —CO—CH$_2$CHOR$^5$—, —CHOH—CH$_2$CHOR$^5$—, a ketal derivative of —CO—CH=CH—, or a ketal derivative of —CO—CH$_2$CH$_2$— and $R^5$ is a lower alkyl group when $R^3$ is a carboxyl group, or Z is —CHOH—CH=CH—, —CHOH-1,2-epoxy-, —CHOH—CH$_2$CHOH—, —CO—CH$_2$CHOR$^5$—, —CHOH—CH$_2$CHOR$^5$—, a ketal derivative of —CO—CH=CH—, or a ketal derivative of —CO—CH$_2$CH$_2$— and $R^5$ is a lower alkyl group when $R^3$ is a —CH$_2$OH.

The lower alkyl group in the formula (1) has 1 to 4 carbon atoms and is preferably a methyl group. Moreover, —CHOH-1,2-epoxy- in the formula (1) is a group represented by the following formula (3):

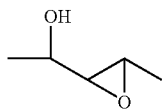

(3)

The ketal derivative in the formula (1) is a non-cyclic ketal or a cyclic ketal, preferably a cyclic ketal. As the cyclic ketal, there may be mentioned those obtained from ethylene glycol, 1,3-propanediol, or 2,2-dimethyl-1,3-propanediol with a carbonyl group.

The invention is a tyrosinase inhibitor comprising a compound represented by the above formula (1), a hyaluronic acid-degrading enzyme inhibitor comprising the compound represented by the formula (1), and an antioxidant comprising the compound represented by the formula (1).

Moreover, the invention is a tyrosinase inhibitor, a hyaluronic acid-degrading enzyme inhibitor, and/or an antioxidant comprising the compound represented by the following formula (2):

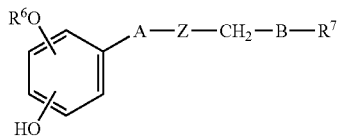

(2)

wherein, $R^6$ is a hydrogen atom, a lower alkyl group, or a protective group of a phenolic hydroxyl group, A is an alkylene group having 1 to 4 carbon atoms, B is an alkylene group having 1 to 12 carbon atoms, $R^7$ is —COOR$^8$ (wherein $R^8$ is a protective group of a carboxyl group), a carboxyl group, or —CH$_2$OH, Z is —CO—CH=CH—, —CHOH—CH=CH—, —CHOH-1,2-epoxy-, —CO—CH$_2$CH$_2$—, —CHOH—CH$_2$CH$_2$—, —CO—CH$_2$CHOH—, —CHOH—CH$_2$CHOH—, —CO—CH$_2$CHOR$^9$—, —CHOH—CH$_2$CHOR$^9$—, a ketal derivative of —CO—CH=CH—, or a ketal derivative of —CO—CH$_2$CH$_2$—, and $R^9$ is a lower alkyl group.

BEST MODE FOR CARRYING OUT THE INVENTION

The following will explain the present invention in more detail.

With Regard to the Compounds Represented by the General Formula (1)

In the formula (1), $R^1$ is a hydrogen atom, a lower alkyl group, or a protective group of a phenolic hydroxyl group. $R^2$ is a hydrogen atom or a protective group of a phenolic hydroxyl group. As the protective group of a phenolic hydroxyl group for $R^1$ and $R^2$, easy introduction and removal of the protective group is preferable and there may be exemplified silyl-type protective groups, acyl-type protective groups, benzyl-type protective groups, ether-type protective groups, and the like. Specifically, a t-butyldimethylsilyl group, a propionyl group, a butyroyl group, an isobutyroyl group, a pivaloyl group, a benzoyl group, a toluoyl group, a benzyl group, a tetrahydropyranyl group, and a methoxymethyl group are suitable.

In the formula (1), A is an alkylene group having 1 to 4 carbon atoms, preferably an ethylene group or a butylene group, and more preferably an ethylene group.

In the formula (1), B is an alkylene group having 1 to 12 carbon atoms, preferably an alkylene group having 1 to 9 carbon atoms, and more preferably an alkylene group having 2 to 6 carbon atoms.

In the formula (1), $R^3$ is —COOR$^4$ (wherein $R^4$ is a protective group of a carboxyl group), a carboxyl group, or —CH$_2$OH. As the protective group of a carboxyl group, a methyl group, an ethyl group, a propyl group, a butyl group, and a benzyl group are suitable. More preferable is a methyl group or an ethyl group.

In the formula (1), Z is —CO—CH=CH—, —CHOH—CH=CH—, —CHOH-1,2-epoxy-, —CO—CH$_2$CH$_2$—, —CHOH—CH$_2$CH$_2$—, —CO—CH$_2$CHOH—, —CHOH—CH$_2$CHOH—, —CO—CH$_2$CHOR$^5$—, —CHOH—CH$_2$CHOR$^5$—, a ketal derivative of —CO—CH=CH—, or a ketal derivative of —CO—CH$_2$CH$_2$— and $R^5$ is a lower alkyl group when $R^3$ is a —COOR$^4$ group. Moreover, in the formula (1), Z is —CO—CH=CH—, —CHOH—CH=CH—, —CHOH-1,2-epoxy-, —CHOH—CH$_2$CH$_2$—, —CHOH—CH$_2$CHOH—, —CO—CH$_2$CHOR$^5$—, —CHOH—CH$_2$CHOR$^5$—, a ketal derivative of —CO—CH=CH—, or a ketal derivative of —CO—CH$_2$CH$_2$— and $R^5$ is a lower alkyl group when $R^3$ is a carboxyl group. Furthermore, in the formula (1), Z is —CHOH—CH=CH—, —CHOH-1,2-epoxy-, —CHOH—CH$_2$CHOH—, —CO—CH$_2$CHOR$^5$—, —CHOH—CH$_2$CHOR$^5$—, a ketal derivative of —CO—CH=CH—, or a ketal derivative of —CO—CH$_2$CH$_2$— and $R^5$ is a lower alkyl group when $R^3$ is a —CH$_2$OH.

With Regard to the Compounds Represented by the General Formula (2)

In the formula (2), $R^6$ is a hydrogen atom, a lower alkyl group, or a protective group of a phenolic hydroxyl group. As the protective group of a phenolic hydroxyl group for $R^6$, easy introduction and removal of the protective group is preferable and there may be exemplified silyl-type protective groups, acyl-type protective groups, benzyl-type protective groups, ether-type protective groups, and the like. Specifically, a t-butyldimethylsilyl group, a propionyl group, a butyroyl group, an isobutyroyl group, a pivaloyl group, a benzoyl group, a toluoyl group, a benzyl group, a tetrahydropyranyl group, and a methoxymethyl group are suitable.

In the formula (2), A is an alkylene group having 1 to 4 carbon atoms, preferably an ethylene group or a butylene group, and more preferably an ethylene group.

In the formula (2), B is an alkylene group having 1 to 12 carbon atoms, preferably an alkylene group having 1 to 9 carbon atoms, and more preferably an alkylene group having 2 to 6 carbon atoms.

In the formula (2), $R^7$ is —COOR$^8$ (wherein $R^8$ is a protective group of a carboxyl group), a carboxyl group, or —CH$_2$OH. As the protective group of a carboxyl group, a methyl group, an ethyl group, a propyl group, a butyl group, and a benzyl group are suitable. More preferable is a methyl group or an ethyl group.

In the formula (2), Z is —CO—CH=CH—, —CHOH—CH=CH—, —CHOH-1,2-epoxy-, —CO—CH$_2$CH$_2$—, —CHOH—CH$_2$CH$_2$—, —CO—CH$_2$CHOH—, —CHOH—CH$_2$CHOH—, —CO—CH$_2$CHOR$^9$—, —CHOH—CH$_2$CHOR$^9$—, a ketal derivative of —CO—CH=CH—, or a ketal derivative of —CO—CH$_2$CH$_2$— and $R^9$ is a lower alkyl group.

Of the compounds represented by the general formula (1), a compound wherein $R^3$ is —COOR$^4$ and Z is —CO—CH═CH— (hereinafter referred to as a compound of the formula (4)) is an intermediate for synthesizing the other compounds represented by the formula (1).

With Regard to Synthetic Methods of the Compound of the Formula (4)

The compound of the formula (4) can be synthesized from a compound represented by the formula (7) (hereinafter referred to as a compound of the formula (7); the following compounds represented by the other formulae are also abbreviated in a similar manner). The compound of the formula (7) is obtained by a reaction of a compound of the formula (5) with a compound of the formula (6) to be mentioned below. Moreover, the compound of the formula (5) can be synthesized from a compound of the formula (10). The compound of the formula (10) is obtained by a reaction of a compound of the formula (8) with a compound of the formula (9) to be mentioned below.

The compound of the formula (4) can be produced by preparing the following compound of the formula (7) starting from the following compound of the formula (5) and the following compound of the formula (6) and further eliminating HX from the following compound of the formula (7).

$$X-CH_2-CH=CH-B-COOR^4 \quad (5)$$

In the formula (5), $R^4$ represents a protective group of a carboxyl group, B represents an alkylene group having 1 to 12 carbon atoms, and X represents a benzenesulfonyl group or a toluenesulfonyl group.

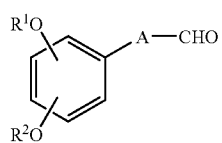

(6)

In the formula (6), $R^1$ is a hydrogen atom, a lower alkyl group, or a protective group of a phenolic hydroxyl group, $R^2$ is a hydrogen atom or a protective group of a phenolic hydroxyl group, and A represents an alkylene group having 1 to 4 carbon atoms.

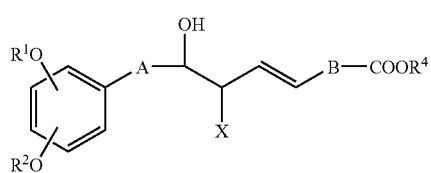

(7)

In the formula (7), $R^1$, $R^2$, $R^4$, A, and B are as defined in the formula (1) and X is as defined in the formula (5).

The compound of the formula (5) can be produced by carrying out a rearrangement reaction of the X group of the compound of the formula (10). The compound of the formula (10) can be produced by reacting the following compound of the formula (8) with an alkylmetal compound, followed by reaction with the following compound of the formula (9).

$$CH_2=CH-CH_2-X \quad (8)$$

In the formula (8), X is as defined in the formula (5).

$$I-B-COOR^4 \quad (9)$$

In the formula (9), $R^4$ and B are as defined in the formula (1) and I is an iodine atom.

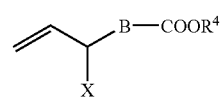

(10)

In the formula (10), $R^4$ and B are as defined in the formula (1) and X is as defined in the formula (5).

In the reaction of the compound of the formula (8) with an alkylmetal compound, the ratio of the alkylmetal compound to the compound of the formula (8) is preferably from 0.7 to 1.3 chemical equivalents, more preferably from 0.9 to 1.1 chemical equivalents.

The temperature of the above reaction is preferably from $-100°$ C. to $0°$ C., more preferably from $-80°$ C. to $-20°$ C. When the reaction temperature is too low, it takes costs to maintain the temperature and when the reaction temperature is too high, side reactions may proceed in some cases.

The reaction of the compound of the formula (8) with an alkylmetal compound is preferably carried out in an aprotic solvent and there can be suitably used tetrahydrofuran, 1,4-dioxane, diethyl ether, 1,2-dimethoxyethane, hexamethylphosphoric triamide, N,N-dimethylpropyleneurea, and mixed solvents thereof.

The reaction time varies depending on conditions but is usually from several minutes to several tens minutes.

As the alkylmetal compound, there may be exemplifed alkyllithium compounds such as n-butyllithium, s-butyllithium, t-butyllithium, and phenyllithium; and Grignard compounds such as n-butylmagnesium chloride, s-butylmagnesium chloride, t-butylmagnesium chloride, n-butylmagnesium bromide, s-butylmagnesium bromide, and t-butylmagnesium bromide, and n-butyllithium, n-butylmagnesium chloride, and n-butylmagnesium bromide can be suitably used. Moreover, alkali metals such as metal lithium and metal sodium may be used instead of the alkylmetal compounds.

The compound of the formula (10) can be obtained by subsequently reacting the reaction product between the compound of the formula (8) and the alkylmetal compound as mentioned above with the above compound of the formula (9).

The temperature of the reaction system at the time when the compound of the formula (9) is added to the above reaction product is preferably from $-100°$ C. to $0°$ C., more preferably from $-80°$ C. to $-20°$ C. When the reaction temperature is too low, it takes costs to maintain the temperature and when the reaction temperature is too high, side reactions may proceed in some cases.

The reaction time varies depending on conditions but is usually from several minutes to several tens minutes.

After completion of the reaction, the compound of the formula (10) can be isolated and purified by a known purification method such as solvent extraction or column chromatography.

The compound of the formula (5) can be obtained by rearranging the X group in the compound of the formula (10).

As a preferred catalyst for the rearrangement reaction of the compound of the formula (10), a palladium catalyst can be exemplified. As the palladium catalyst, there may be suitably used tetrakistriphenylphosphine palladium(0), a tris (dibenzylideneacetone) dipalladium(0) chloroform adduct, a palladium(II) chloride/triphenylphosphine mixture, a palladium(II) acetate/triphenylphosphine mixture, a palladium (II) acetate/tributylphosphine mixture, or the like is suitably used. The amount of the palladium catalyst to be used is preferably from 0.0001 to 1 mol, more preferably from 0.001 to 0.1 mol relative to 1 mol of the compound of the formula (10). When the amount of the catalyst is too small, the progress of the reaction may be sometimes retarded and when it is too large, it takes labor to remove the catalyst in some cases.

The rearrangement reaction is preferably carried out in the presence of a solvent and there can be used tetrahydrofuran, 1,4-dioxane, diethyl ether, 1,2-dimethoxyethane, toluene, acetonitrile, chloroform, dichloromethane, 1,2-dichloroethane, hexamethylphosphoric triamide, N,N-dimethylpropyleneurea, methanol, ethanol, isopropyl alcohol, ethylene glycol, glycerin, and mixed solvents thereof. Of these, a mixed solvent of tetrahydrofuran and methanol is suitable.

Suitably, the reaction temperature of the rearrangement reaction is preferably in the range of 0° C. to 120° C., more preferably 20° C. to 100° C. The reaction time varies depending on conditions but is usually from several hours to several tens hours.

After completion of the reaction, the compound of the formula (5) can be obtained by a known purification method such as solvent extraction or column chromatography.

The compound of the formula (6) can be synthesized according to the method described in literatures such as G. Solladie, et al., *J. Org. Chem.*, 58, 2181 (1993).

In the compound of the formula (6), $R^1$ represents a hydrogen atom, a lower alkyl group, or a protective group of a phenolic hydroxyl group and $R^2$ represents a hydrogen atom or a protective group of a phenolic hydroxyl group. As the lower alkyl group of $R^1$ in the formula (6) preferably has 1 to 3 carbon atoms and is more preferably a methyl group.

As the protective group of a phenolic hydroxyl group for $R^1$ and $R^2$ in the formula (6), easy introduction and removal of the protective group is preferable and there may be exemplified silyl-type protective groups, acyl-type protective groups, benzyl-type protective groups, ether-type protective groups, and the like. Specifically, a t-butyldimethylsilyl group, a propionyl group, a butyroyl group, an isobutyroyl group, a pivaloyl group, a benzoyl group, a toluoyl group, a benzyl group, a tetrahydropyranyl group, and a methoxymethyl group are suitable.

In the formula (6), A is an alkylene group having 1 to 4 carbon atoms, preferably an ethylene group or a butylene group, and more preferably an ethylene group.

The compound of the formula (7) which is a compound for obtaining the compound of the formula (4) can be produced by reacting the compound of the formula (5) producible by the above method or the like with an alkylmetal compound, followed by reaction with the compound of the formula (6).

As the alkylmetal compound, a compound which exerts no adverse effects on the protective group of the carboxyl group in the compound of the formula (5) is preferable and, for example, there can be preferably used t-butyllithium, lithium diisopropylamide, or lithium bis(trimethylsilyl)amide.

Basically, the amount of the alkylmetal compound to be used is preferably from 0.7 to 1.3 chemical equivalents, more preferably from 0.9 to 1.1 chemical equivalents relative to the compound of the formula (5).

The above reaction is preferably carried out in an aprotic solvent and there may be suitably used tetrahydrofuran, 1,4-dioxane, diethyl ether, 1,2-dimethoxyethane, hexamethylphosphoric triamide, N,N-dimethylpropyleneurea, and mixed solvents thereof.

The temperature of the reaction of the compound of the formula (5) with the alkylmetal compound is preferably from −80° C. to 25° C., more preferably −50° C. to 0° C. The reaction time is usually from several minutes to several hours.

The compound of the formula (7) can be produced by subsequently reacting the reaction product between the compound of the formula (5) and the alkylmetal compound as mentioned above with the compound of the formula (6).

The temperature of the reaction system at the time when the compound of the formula (6) is added to the reaction product is preferably from −100° C. to 25° C., suitably from −80° C. to 0° C. The reaction time is suitably from several minutes to several hours.

After completion of the reaction, the compound of the formula (7) can be isolated and purified by a known purification method such as solvent extraction or column chromatography.

The compound of the formula (4) in the invention can be synthesized by treating the compound of the formula (7) produced by the above method or the like with a basic compound in the presence of a metal catalyst which forms a π-allyl complex.

As the metal catalyst which forms a π-allyl complex, a palladium catalyst can be suitably used. Specifically, there may be exemplified tetrakistriphenylphosphine palladium (0), a tris(dibenzylideneacetone) dipalladium(0) chloroform adduct, a palladium(II) chloride/triphenylphosphine mixture, a palladium(II) acetate/triphenylphosphine mixture, a palladium(II) acetate/tributylphosphine mixture, and the like. The amount of the palladium catalyst to be used is preferably from 0.0001 to 1 mol, more preferably from 0.001 to 0.1 mol relative to 1 mol of the compound of the formula (7).

As the above basic compound, tertiary amines such as triethylamine, diisopropylethylamine, N-methylimidazole, and pyridine are suitable. The amount of the basic compound to be used is 0.9 mol or more, suitably from 1.0 mol to 10 mol relative to 1 mol of the compound of the formula (7).

The above reaction is preferably carried out in the presence of a solvent and there may be used tetrahydrofuran, 1,4-dioxane, diethyl ether, 1,2-dimethoxyethane, acetonitrile, chloroform, dichloromethane, 1,2-dichloroethane, hexamethylphosphoric triamide, N,N-dimethylpropyleneurea, methanol, ethanol, isopropyl alcohol, ethylene glycol, glycerin, and mixed solvents thereof. Of these, a mixed solvent of 1,2-dichloroethane and an alcohol is suitable.

Suitably, the reaction temperature is preferably from room temperature to 150° C., more preferably from 50° C. to 120° C.

The reaction time is suitably from several hours to several tens hours.

After completion of the reaction, the compound of the formula (4) can be obtained by a known purification method such as solvent extraction or column chromatography.

Of the compounds of the formula (4), a compound wherein $R^2$ is a hydrogen atom represents the same compound as the compound represented by the general formula (2) of the invention wherein $R^7$ is —COOR$^8$ and Z is —CO—CH=CH—. When $R^2$ in the compound of the formula (4) is a protective group of a phenolic hydroxyl group, the compound wherein $R^2$ is a hydrogen atom can be obtained by removing the protective group of a phenolic hydroxyl group.

The method for removing the protective group of a phenolic hydroxyl group can be performed in accordance with methods well known in the field of organic synthetic chemistry, e.g., methods described in T. W. Greene., "Protective Groups in Organic Synthesis", John Wiley & Sons.

Of the compounds represented by the general formula (1) of the invention, a compound wherein $R^3$ is —COOR$^4$ and Z is —CHOH—CH=CH— (hereinafter referred to as a compound of the formula (11)) can be produced by reducing an oxo group of the compound of the formula (4) mentioned above with a metal-hydrogen complex compound or the like into a hydroxyl group.

Of the compounds represented by the general formula (1) of the invention, a compound wherein $R^3$ is —COOR$^4$ and Z is —CHOH-1,2-epoxy- (hereinafter referred to as a compound of the formula (12)) can be produced by epoxidizing the compound of the formula (11).

The following shows the conversion of the formula (4) into the formula (11) and the formula (12).

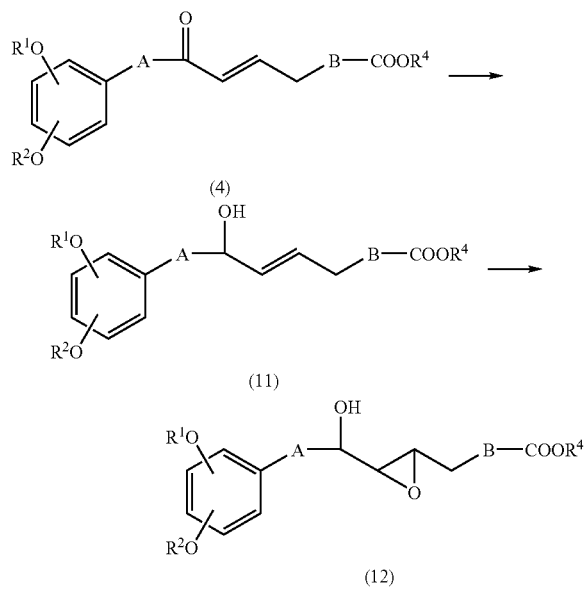

$R^1$, $R^2$, $R^4$, A, and B in the formula (11) and the formula (12) are as defined in the formula (1).

As the metal-hydrogen complex compound at the time when the ketone in the compound of the formula (4) is reduced into a hydroxyl group, lithium borohydride, sodium borohydride, or the like can be preferably used. Moreover, the reaction can be also carried out under the conditions of using sodium borohydride and cerium(III) chloride in combination. In the reaction, preferable is the conditions of using sodium borohydride and cerium(III) chloride in combination. In the reaction, the ratio of the metal-hydrogen complex compound to the compound of the formula (4) is preferably from 0.5 to 10 chemical equivalents, more preferably from 1 to 2 chemical equivalents. In the case that the reduction reaction is carried out under the conditions of using sodium borohydride and cerium(III) chloride in combination, the amount of cerium(III) chloride to be used is preferably from 0.01 to 5 chemical equivalents, more preferably from 0.1 to 3 chemical equivalents relative to the compound of the formula (4).

The above reaction is preferably carried out in the presence of a solvent and there may be used tetrahydrofuran, 1,4-dioxane, diethyl ether, 1,2-dimethoxyethane, acetonitrile, methanol, ethanol, isopropyl alcohol, and mixed solvents thereof.

Suitably, the reaction temperature at the time when the compound of the formula (11) is produced is preferably from −100° C. to 100° C., more preferably −78° C. to room temperature. The reaction time is suitably from several minutes to several hours. After completion of the reaction, the compound of the formula (11) can be obtained by a known purification method such as solvent extraction or column chromatography.

Of the compounds of the formula (11), a compound wherein $R^2$ is a hydrogen atom represents the same compound as the compound represented by the general formula (2) of the invention wherein $R^7$ is —COOR$^8$ and Z is —CHOH—CH=CH—. When $R^2$ in the compound of the formula (11) is a protective group of a phenolic hydroxyl group, the compound wherein $R^2$ is a hydrogen atom can be obtained by removing the protective group of a phenolic hydroxyl group.

As the epoxidizing agent at the time when the compound of the formula (12) is produced from the compound of the formula (11), there can be suitably used peracids such as peracetic acid, trifluoroperacetic acid, perbenzoic acid, and m-chloroperbenzoic acid and peroxides such as hydrogen peroxide and t-butyl hydroperoxide. The amount of the peracids and peroxides to be used is preferably from 1 to 10 chemical equivalents, more preferably from 1.1 to 2 chemical equivalents.

The above reaction is preferably carried out in the presence of a solvent and there may be used dichloromethane, chloroform, 1,2-dichloroethane, tetrahydrofuran, 1,4-dioxane, diethyl ether, 1,2-dimethoxyethane, acetonitrile, toluene, water, and mixed solvents thereof.

Suitably, the reaction temperature at the time when the compound of the formula (12) is produced is preferably from −100° C. to 100° C., more preferably −78° C. to 50° C. The reaction time is suitably from several tens minutes to several hours. After completion of the reaction, the compound of the formula (12) can be obtained by a known purification method such as solvent extraction or column chromatography.

Of the compounds of the formula (12), a compound wherein $R^2$ is a hydrogen atom represents the same compound as the compound represented by the general formula (2) of the invention wherein $R^7$ is —COOR$^8$ and Z is —CHOH-1,2-epoxy-. When $R^2$ in the compound of the formula (12) is a protective group of a phenolic hydroxyl group, the compound wherein $R^2$ is a hydrogen atom can be obtained by removing the protective group of a phenolic hydroxyl group.

Of the compounds represented by the general formula (1) of the invention, a compound wherein $R^3$ is —COOR$^4$ and Z is —CO—CH$_2$CH$_2$— (hereinafter referred to as a compound of the formula (13)) can be produced by catalytically hydrogenating the compound of the formula (4).

Of the compounds represented by the general formula (1), a compound wherein $R^3$ is —COOR$^4$ and Z is —CHOH—CH$_2$CH$_2$— (hereinafter referred to as a compound of the formula (14)) can be produced by reducing the compound of the formula (13) with a metal-hydrogen complex compound.

The following shows the conversion of the formula (4) into the formula (13) and the formula (14).

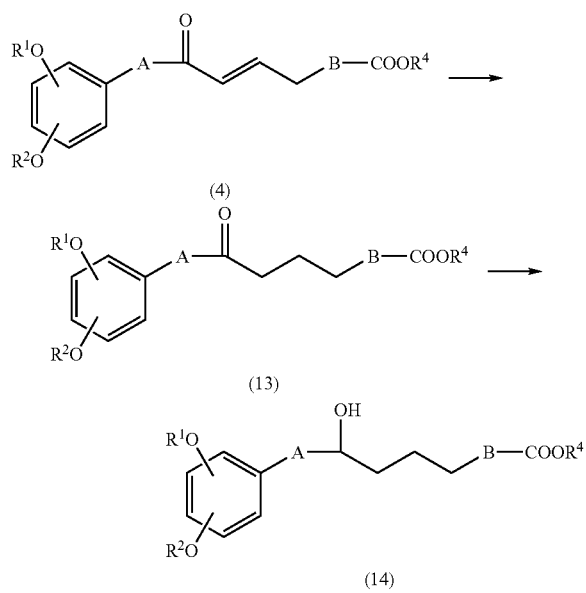

R$^1$, R$^2$, R$^4$, A, and B in the formula (13) and the formula (14) are as defined in the formula (1).

At the time when the compound of the formula (13) is produced, it is preferable to use a metal catalyst such as palladium-carbon, platinum oxide (IV), Raney-nickel, platinum black, rhodium-aluminum oxide, triphenylphosphin-rhodium chloride, palladium-barium sulfate, or the like and render the inside of the reaction vessel under a hydrogen atmosphere. In the reaction, the ratio of the metal catalyst to the compound of the formula (4) is preferably from 0.01 to 100% by weight, more preferably from 0.1 to 10% by weight.

The production of the compound of the formula (13) is preferably carried out in the presence of a solvent and there can be used methanol, ethanol, n-propyl alcohol, isopropyl alcohol, n-butyl alcohol, t-butyl alcohol, n-pentane, n-hexane, toluene, ethyl acetate, acetic acid, tetrahydrofuran, 1,4-dioxane, diethyl ether, 1,2-dimethoxyethane, acetonitrile, N,N-dimethylformamide, N,N-dimethylpropyleneurea, dimethyl sulfoxide, water, and mixed solvents thereof.

Suitably, the reaction temperature at the time when the compound of the formula (13) is produced is preferably from 0° C. to 100° C., more preferably room temperature to 50° C. The reaction time is suitably from several tens minutes to several tens hours. After completion of the reaction, the compound of the formula (13) can be obtained by a known purification method such as solvent extraction or column chromatography.

Of the compounds of the formula (13), a compound wherein R$^2$ is a hydrogen atom represents the same compound as the compound represented by the general formula (2) of the invention wherein R$^7$ is —COOR$^8$ and Z is —CO—CH$_2$CH$_2$—. When R$^2$ in the compound of the formula (13) is a protective group of a phenolic hydroxyl group, the compound wherein R$^2$ is a hydrogen atom can be obtained by removing the protective group of a phenolic hydroxyl group.

As the metal-hydrogen complex compound at the time when the compound of the formula (14) is produced, preferable is one which does not exert an adverse effect on the protective group of a carboxyl group and lithium borohydride, sodium borohydride, or the like can be preferably used. More preferable is sodium borohydride. In the reaction, the ratio of the metal-hydrogen complex compound to the compound of the formula (13) is preferably from 0.5 to 10 chemical equivalents, more preferably from 1 to 2 chemical equivalents.

The production of the compound of the formula (14) is preferably carried out in the presence of a solvent and there may be used tetrahydrofuran, 1,4-dioxane, diethyl ether, 1,2-dimethoxyethane, acetonitrile, methanol, ethanol, isopropyl alcohol, and mixed solvents thereof.

Suitably, the reaction temperature at the time when the compound of the formula (14) is produced is preferably from –20° C. to 100° C., more preferably 0° C. to room temperature. The reaction time is suitably from several minutes to several hours. After completion of the reaction, the compound of the formula (14) can be obtained by a known purification method such as solvent extraction or column chromatography.

Of the compounds of the formula (14), a compound wherein R$^2$ is a hydrogen atom represents the same compound as the compound represented by the general formula (2) of the invention wherein R$^7$ is —COOR$^8$ and Z is —CHOH—CH$_2$CH$_2$—. When R$^2$ in the compound of the formula (14) is a protective group of a phenolic hydroxyl group, the compound wherein R$^2$ is a hydrogen atom can be obtained by removing the protective group of a phenolic hydroxyl group.

Of the compounds represented by the general formula (1) of the invention, a compound wherein R$^3$ is —COOR$^4$ and Z is —CO—CH$_2$CHOH— (hereinafter referred to as a compound of the formula (15)) can be produced by adding water molecule to the compound of the formula (4).

Moreover, of the compounds represented by the general formula (1), a compound wherein R$^3$ is —COOR$^4$ and Z is —CHOH—CH$_2$CHOH— (hereinafter referred to as a compound of the formula (16)) can be produced by reducing the compound of the formula (15) with a metal-hydrogen complex compound.

The following shows the conversion of the formula (4) into the formula (15) and the formula (16).

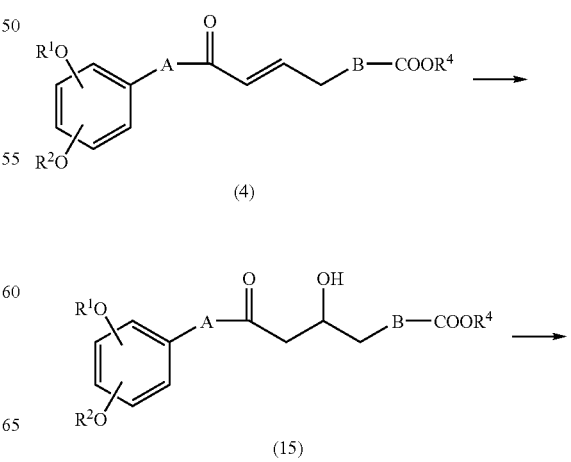

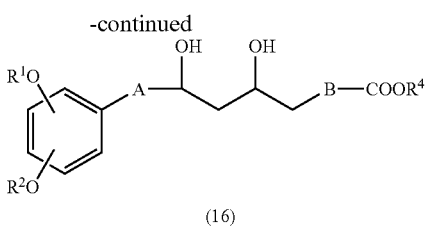

(16)

$R^1$, $R^2$, $R^4$, A, and B in the formula (15) and the formula (16) are as defined in the formula (1).

At the time when water molecule is added to the compound of the formula (4) for obtaining the formula (15), it is preferable to use a metal hydroxide such as sodium hydroxide or potassium hydroxide as an aqueous solution. The amount of the metal hydroxide to be used is preferably from 1 to 10 chemical equivalents, more preferably from 2 to 5 chemical equivalents relative to the compound of the formula (4) Moreover, a phase-transfer catalyst may be also used in combination at that time. As the phase-transfer catalyst, there may be preferably used quaternary ammonium salts such as tetrabutylammonium bromide, benzyltributylammonium bromide, and trioctylmethylammonium bromide. The amount of the phase-transfer catalyst to be used is preferably from 0.001 to 1 chemical equivalents, more preferably from 0.01 to 0.2 chemical equivalents relative to the compound of the formula (4).

The above reaction is preferably carried out in the presence of a solvent and there may be used tetrahydrofuran, 1,4-dioxane, diethyl ether, 1,2-dimethoxyethane, acetonitrile, toluene, chloroform, dichloromethane, 1,2-dichloroethane, t-butyl alcohol, N,N-dimethylformamide, N,N-dimethylpropyleneurea, dimethyl sulfoxide, and mixed solvents thereof.

Suitably, the reaction temperature at the time when the compound of the formula (15) is produced is preferably from 0° C. to 150° C., more preferably room temperature to 100° C. The reaction time is suitably from several hours to several tens hours. After completion of the reaction, the compound of the formula (15) can be obtained by a known purification method such as solvent extraction or column chromatography.

In this connection, at the time of the above addition reaction of water molecule, in the case that $R^4$ is an alkyl group such as a methyl group or an ethyl group, hydrolysis occurs and there is a possibility that $R^4$ is removed. In such a case, esterification may be carried out after isolation and purification to synthesize the compound of the formula (15). As the conditions for esterification, the reaction can be carried out in accordance with methods well known in the field of organic synthetic chemistry, e.g., methods described in T. W. Greene., "Protective Groups in Organic Synthesis", John Wiley & Sons.

Of the compounds of the formula (15), a compound wherein $R^2$ is a hydrogen atom represents the same compound as the compound represented by the general formula (2) of the invention wherein $R^7$ is —COOR$^8$ and Z is —CO—CH$_2$CHOH—. When $R^2$ in the compound of the formula (15) is a protective group of a phenolic hydroxyl group, the compound wherein $R^2$ is a hydrogen atom can be obtained by removing the protective group of a phenolic hydroxyl group.

The reducing agent to be used at the time when the compound of the formula (16) is produced is the same as the reducing agent used at the time when the compound of the formula (14) is produced from the compound of the formula (13) and is preferably sodium borohydride.

The solvent to be used at the time when the compound of the formula (16) is produced is the same as the solvent used at the time when the compound of the formula (14) is produced from the compound of the formula (13).

Suitably, the reaction temperature at the time when the compound of the formula (16) is produced is preferably from −20° C. to 100° C., more preferably 0° C. to room temperature. The reaction time is suitably from several minutes to several hours. After completion of the reaction, the compound of the formula (16) can be obtained by a known purification method such as solvent extraction or column chromatography.

Of the compounds of the formula (16), a compound wherein $R^2$ is a hydrogen atom represents the same compound as the compound represented by the general formula (2) of the invention wherein $R^7$ is —COOR$^8$ and Z is —CHOH—CH$_2$CHOH—. When $R^2$ in the compound of the formula (16) is a protective group of a phenolic hydroxyl group, the compound wherein $R^2$ is a hydrogen atom can be obtained by removing the protective group of a phenolic hydroxyl group.

Of the compounds represented by the general formula (1) of the invention, a compound wherein $R^3$ is —COOR$^4$ and Z is —CO—CH$_2$CHOR$^5$— (hereinafter referred to as a compound of the formula (17)) can be produced by adding a lower alcohol in the presence of a basic compound to the compound of the formula (4).

Moreover, of the compounds represented by the general formula (1), a compound wherein $R^3$ is —COOR$^4$ and Z is —CHOH—CH$_2$CHOR$^5$— (hereinafter referred to as a compound of the formula (18)) can be produced by reducing the compound of the formula (17) with a metal-hydrogen complex compound.

The following shows the conversion of the formula (4) into the formula (17) and the formula (18).

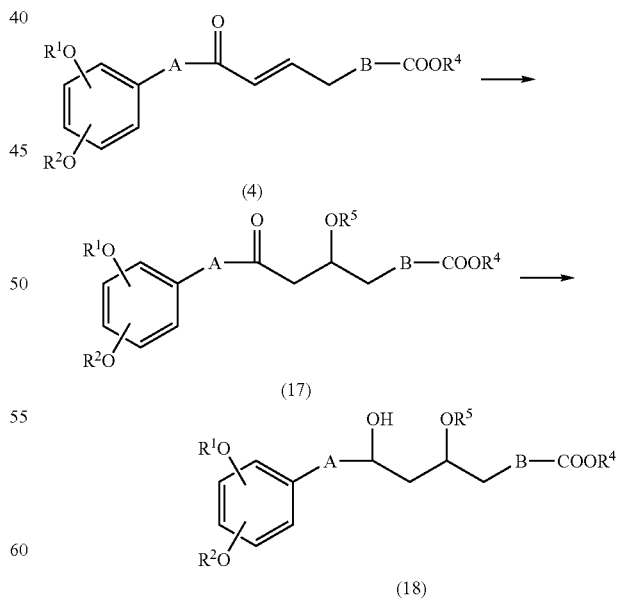

$R^1$, $R^2$, $R^4$, A, and B in the formula (17) and the formula (18) are as defined in the formula (1).

As the basic substance to be used at the time when the compound of the formula (17) is produced from the compound of the formula (4), it is preferable to use alkali metal hydroxides such as sodium hydroxide and potassium hydroxide. The amount of the alkali metal hydroxide to be used is preferably from 1 to 10 chemical equivalents, more preferably from 2 to 5 chemical equivalents relative to the compound of the formula (4). The lower alcohol to be used at the time when the compound of the formula (17) is produced from the compound of the formula (4), there may be mentioned methanol, ethanol, n-propyl alcohol, isopropyl alcohol, n-butyl alcohol, and the like. Moreover, a lower alcohol may be used as a solvent.

Suitably, the reaction temperature at the time when the compound of the formula (17) is produced from the compound of the formula (4) is preferably from 0° C. to 150° C., more preferably room temperature to 100° C. The reaction time is suitably from several hours to several tens hours. After completion of the reaction, the compound of the formula (17) can be obtained by a known purification method such as solvent extraction or column chromatography.

In this connection, at the time of the above addition reaction of the lower alcohol, in the case that $R^4$ is an alkyl group such as a methyl group or an ethyl group, hydrolysis occurs and there is a possibility that $R^4$ is removed. In such a case, esterification may be carried out after isolation and purification to synthesize the compound of the formula (17). As the conditions for esterification, the reaction can be carried out in accordance with methods well known in the field of organic synthetic chemistry, e.g., methods described in T. W. Greene., "Protective Groups in Organic Synthesis", John Wiley & Sons.

Of the compounds of the formula (17), a compound wherein $R^2$ is a hydrogen atom represents the same compound as the compound represented by the general formula (2) of the invention wherein $R^7$ is —COOR$^8$ and Z is —CO—CH$_2$CHOR$^5$—. When $R^2$ in the compound of the formula (17) is a protective group of a phenolic hydroxyl group, the compound wherein $R^2$ is a hydrogen atom can be obtained by removing the protective group of a phenolic hydroxyl group.

The reducing agent to be used at the time when the compound of the formula (18) is produced from the compound of the formula (17) is the same as the reducing agent used at the time when the compound of the formula (14) is produced from the compound of the formula (13) and is preferably sodium borohydride.

The solvent to be used at the time when the compound of the formula (18) is produced from the compound of the formula (17) is produced is the same as the solvent used at the time when the compound of the formula (14) is produced from the compound of the formula (13).

Suitably, the reaction temperature at the time when the compound of the formula (18) is produced from the compound of the formula (17) is preferably from −20° C. to 100° C., more preferably 0° C. to room temperature. The reaction time is suitably from several minutes to several hours. After completion of the reaction, the compound of the formula (18) can be obtained by a known purification method such as solvent extraction or column chromatography.

Of the compounds of the formula (18), a compound wherein $R^2$ is a hydrogen atom represents the same compound as the compound represented by the general formula (2) of the invention wherein $R^7$ is —COOR$^8$ and Z is —CHOH—CH$_2$CHOR$^5$—. When $R^2$ in the compound of the formula (18) is a protective group of a phenolic hydroxyl group, the compound wherein $R^2$ is a hydrogen atom can be obtained by removing the protective group of a phenolic hydroxyl group.

Of the compounds represented by the general formula (1) of the invention, a compound wherein $R^3$ is —COOR$^4$ and Z is a ketal derivative of —CO—CH=CH— (hereinafter referred to as a compound of the formula (19)) can be produced by converting the compound of the formula (4) into a non-cyclic ketal or cyclic ketal thereof.

In a similar manner, of the compounds represented by the general formula (1), a compound wherein $R^3$ is —COOR$^4$ and Z is a ketal derivative of —CO—CH$_2$CH$_2$— (hereinafter referred to as a compound of the formula (20)) can be produced from the compound of the formula (13).

The following shows the conversion of the formula (4) into the formula (19) and the formula (20).

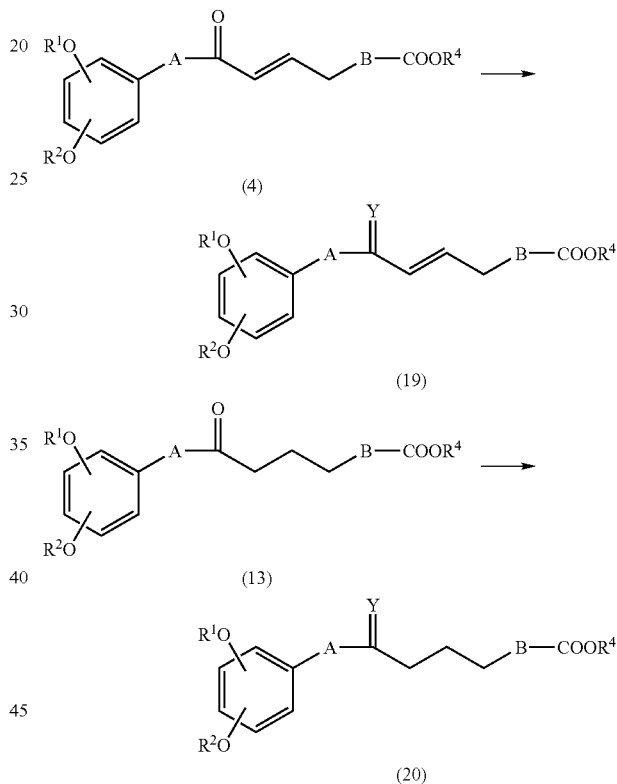

$R^1$, $R^2$, $R^4$, A, and B in the formula (19) and the formula (20) are as defined in the formula (1), and Y represents a non-cyclic ketal or a cyclic ketal.

As the non-cyclic ketal of the formula (19) and the formula (20), there may be mentioned dimethyl ketals, diacetyl ketals, or the like. As the cyclic ketal of the formula (19) and the formula (20), there may be mentioned those obtained from ethylene glycol, 1,3-propanediol, or 2,2-dimethyl-1,3-propanediol with a carbonyl group.

The ketalization of the formula (4) can be carried out in accordance with known methods well known in the field of organic synthetic chemistry, e.g., methods described in T. W. Greene., "Protective Groups in Organic Synthesis", John Wiley & Sons.

Of the compounds of the formula (19), a compound wherein $R^2$ is a hydrogen atom represents the same compound as the compound represented by the general formula (2) of the invention wherein $R^7$ is —COOR$^8$ and Z is a ketal derivative of —CO—CH=CH—. Moreover, of the compounds of the formula (20), a compound wherein $R^2$ is a hydrogen atom represents the same compound as the compound represented by the general formula (2) of the invention wherein $R^7$ is —COOR$^8$ and Z is a ketal derivative of —CO—CH$_2$—CH$_2$—.

When $R^2$ in the compound of the formula (19) or the compound of the formula (20) is a protective group of a phenolic hydroxyl group, the compound wherein $R^2$ is a hydrogen atom can be obtained by removing the protective group of a phenolic hydroxyl group.

Of the compounds represented by the general formula (1) of the invention, a compound wherein $R^3$ is a carboxyl group and Z is —CO—CH=CH— (hereinafter referred to as a compound of the formula (21)) can be produced by removing the protective group of the carboxyl group in the above compound of the formula (4). See, the following scheme.

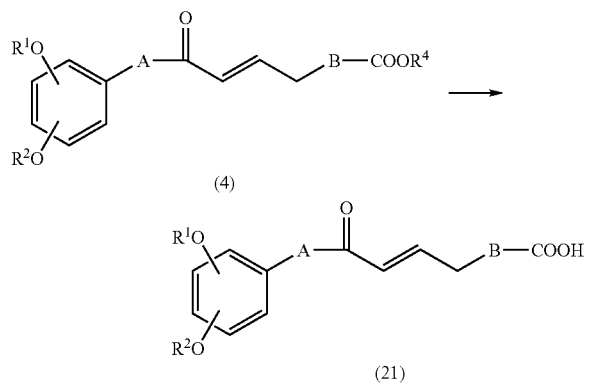

$R^1$, $R^2$, $R^4$, A, and B in the formula (21) are as defined in the formula (1).

Similarly, of the compounds represented by the general formula (1) of the invention, a compound wherein $R^3$ is a carboxyl group and Z is —CHOH—CH=CH— (hereinafter referred to as a compound of the formula (22)) can be synthesized from the compound of the formula (11) mentioned above. See, the following scheme.

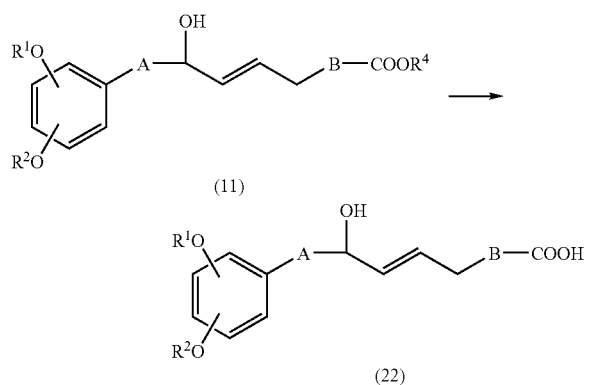

$R^1$, $R^2$, $R^4$, A, and B in the formula (22) are as defined in the formula (1).

Similarly, of the compounds represented by the general formula (1) of the invention, a compound wherein $R^3$ is a carboxyl group and Z is —CHOH-1,2-epoxy- (hereinafter referred to as a compound of the formula (23)) can be synthesized from the compound of the formula (12) mentioned above. See, the following scheme.

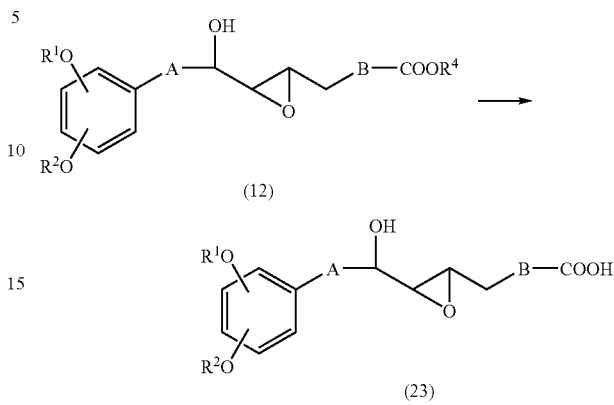

$R^1$, $R^2$, $R^4$, A, and B in the formula (23) are as defined in the formula (1).

Similarly, of the compounds represented by the general formula (1) of the invention, a compound wherein $R^3$ is a carboxyl group and Z is —CHOH—CH$_2$—CH$_2$— (hereinafter referred to as a compound of the formula (24)) can be synthesized from the compound of the formula (14) mentioned above. See, the following scheme.

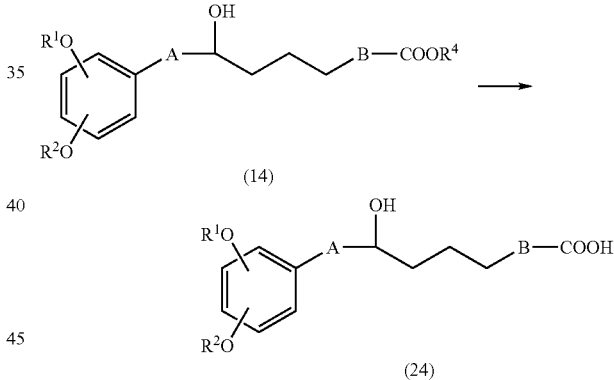

$R^1$, $R^2$, $R^4$, A, and B in the formula (24) are as defined in the formula (1).

Similarly, of the compounds represented by the general formula (1) of the invention, a compound wherein $R^3$ is a carboxyl group and Z is —CHOH—CH$_2$CHOH— (hereinafter referred to as a compound of the formula (25)) can be synthesized from the compound of the formula (16) mentioned above. See, the following scheme.

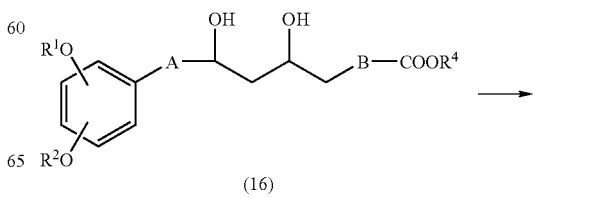

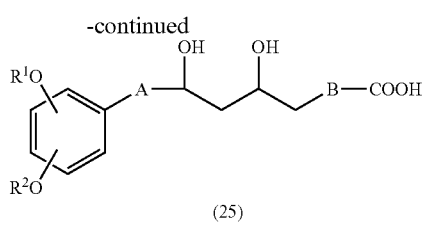

(25)

$R^1$, $R^2$, $R^4$, A, and B in the formula (25) are as defined in the formula (1).

Similarly, of the compounds represented by the general formula (1) of the invention, a compound wherein $R^3$ is a carboxyl group and Z is —CO—$CH_2$CHOR$^5$— (hereinafter referred to as a compound of the formula (26)) can be synthesized from the compound of the formula (17) mentioned above. See, the following scheme.

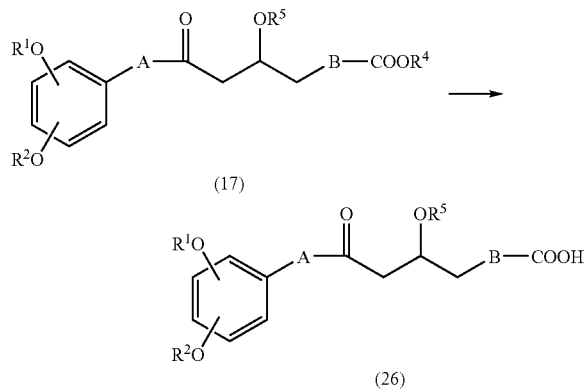

$R^1$, $R^2$, $R^4$, $R^5$, A, and B in the formula (26) are as defined in the formula (1).

Similarly, of the compounds represented by the general formula (1) of the invention, a compound wherein $R^3$ is a carboxyl group and Z is —CHOH—$CH_2$CHOR$^5$— (hereinafter referred to as a compound of the formula (27)) can be synthesized from the compound of the formula (18) mentioned above. See, the following scheme.

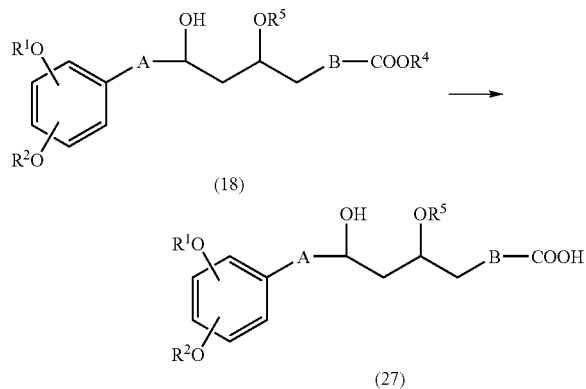

$R^1$, $R^2$, $R^4$, $R^5$, A, and B in the formula (27) are as defined in the formula (1).

Similarly, of the compounds represented by the general formula (1) of the invention, a compound wherein $R^3$ is a carboxyl group and Z is a ketal derivative of —CO—CH=CH— (hereinafter referred to as a compound of the formula (28)) can be synthesized from the compound of the formula (19) mentioned above. See, the following scheme.

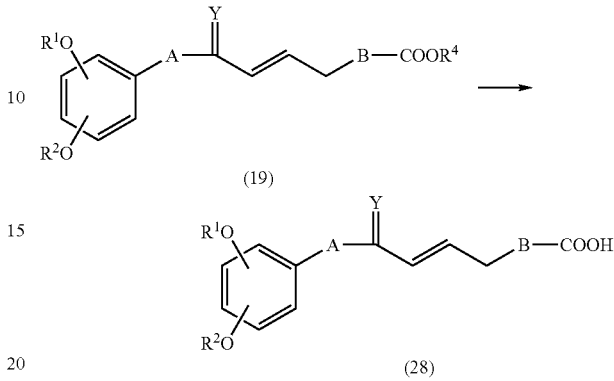

$R^1$, $R^2$, $R^4$, A, B, and Y in the formula (28) are as defined in the formula (1).

Similarly, of the compounds represented by the general formula (1) of the invention, a compound wherein $R^3$ is a carboxyl group and Z is a ketal derivative of —CO—$CH_2CH_2$— (hereinafter referred to as a compound of the formula (29)) can be synthesized from the compound of the formula (20) mentioned above. See, the following scheme.

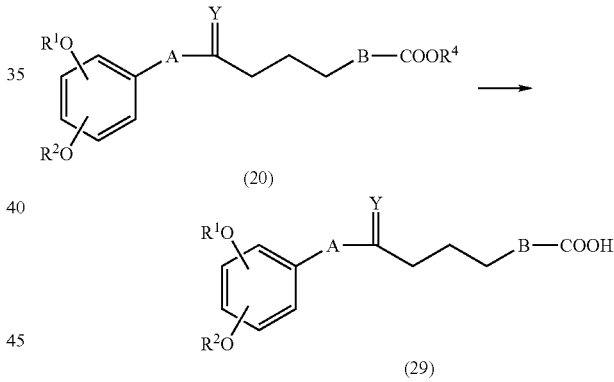

$R^1$, $R^2$, $R^4$, A, B, and Y in the formula (29) are as defined in the formula (1).

The reaction conditions for removing the protective groups from these compounds wherein the carboxyl group is protected (protected compounds) vary depending on the kind of the protective groups used. For example, the protective group of the carboxyl group is an ethyl group, it can be removed in the presence of an alkali catalyst such as sodium hydroxide or potassium hydroxide.

The amount of the above alkali catalyst to be used varies depending on the structures of $R^1$, $R^2$, and $R^4$ of the protected compounds and the kind of the alkali catalysts but is preferably from 1 to 10 chemical equivalents, more preferably from 2 to 5 chemical equivalents relative to the protected compound. When the amount of the above alkali catalyst to be used is too small, the progress of the reaction is slow in some cases and, when the amount is too large, a large amount of a neutralizing agent is necessary for treatment after the reaction.

In the above reaction, a solvent may be used and there may be suitably used tetrahydrofuran, 1,4-dioxane, diethyl ether, 1,2-dimethoxyethane, N,N-dimethylformamide, N,N-dimethylpropyleneurea, water, methanol, ethanol, isopropyl alcohol, t-butyl alcohol, and mixed solvents thereof.

The reaction temperature of the above reaction is preferably from −20° C. to 80° C., more preferably from 0° C. to 50° C. When the reaction temperature is too low, the progress of the reaction is low in some cases and when the reaction temperature is too high, side reactions may proceed in some cases. The reaction time varies depending on conditions but is usually from several tens minutes to several hours. After completion of the reaction, the individual aimed compounds can be obtained by a known purification method such as solvent extraction or column chromatography.

A compound of the compounds of the formula (21) wherein $R^2$ is a hydrogen atom represents the same compound as the compound represented by the general formula (2) of the invention wherein $R^7$ is a carboxyl group and Z is —CO—CH=CH—. When $R^2$ in the compound of the formula (21) is a protective group of a phenolic hydroxyl group, the compound wherein $R^2$ is a hydrogen atom can be obtained by removing the protective group of a phenolic hydroxyl group.

A compound of the compounds of the formula (22) wherein $R^2$ is a hydrogen atom represents the same compound as the compound represented by the general formula (2) of the invention wherein $R^7$ is a carboxyl group and Z is —CHOH—CH=CH—. When $R^2$ in the compound of the formula (22) is a protective group of a phenolic hydroxyl group, the compound wherein $R^2$ is a hydrogen atom can be obtained by removing the protective group of a phenolic hydroxyl group.

A compound of the compounds of the formula (23) wherein $R^2$ is a hydrogen atom represents the same compound as the compound represented by the general formula (2) of the invention wherein $R^7$ is a carboxyl group and Z is —CHOH-1,2-epoxy-. When $R^2$ in the compound of the formula (23) is a protective group of a phenolic hydroxyl group, the compound wherein $R^2$ is a hydrogen atom can be obtained by removing the protective group of a phenolic hydroxyl group.

A compound of the compounds of the formula (24) wherein $R^2$ is a hydrogen atom represents the same compound as the compound represented by the general formula (2) of the invention wherein $R^7$ is a carboxyl group and Z is —CHOH—CH$_2$—CH$_2$—. When $R^2$ in the compound of the formula (24) is a protective group of a phenolic hydroxyl group, the compound wherein $R^2$ is a hydrogen atom can be obtained by removing the protective group of a phenolic hydroxyl group.

A compound of the compounds of the formula (25) wherein $R^2$ is a hydrogen atom represents the same compound as the compound represented by the general formula (2) of the invention wherein $R^7$ is a carboxyl group and Z is —CHOH—CH$_2$CHOH—. When $R^2$ in the compound of the formula (25) is a protective group of a phenolic hydroxyl group, the compound wherein $R^2$ is a hydrogen atom can be obtained by removing the protective group of a phenolic hydroxyl group.

A compound of the compounds of the formula (26) wherein $R^2$ is a hydrogen atom represents the same compound as the compound represented by the general formula (2) of the invention wherein $R^7$ is a carboxyl group and Z is —CO—CH$_2$CHOR$^5$—. When $R^2$ in the compound of the formula (26) is a protective group of a phenolic hydroxyl group, the compound wherein $R^2$ is a hydrogen atom can be obtained by removing the protective group of a phenolic hydroxyl group.

A compound of the compounds of the formula (27) wherein $R^2$ is a hydrogen atom represents the same compound as the compound represented by the general formula (2) of the invention wherein $R^7$ is a carboxyl group and Z is —CHOH—CH$_2$CHOR$^5$—. When $R^2$ in the compound of the formula (27) is a protective group of a phenolic hydroxyl group, the compound wherein $R^2$ is a hydrogen atom can be obtained by removing the protective group of a phenolic hydroxyl group.

A compound of the compounds of the formula (28) wherein $R^2$ is a hydrogen atom represents the same compound as the compound represented by the general formula (2) of the invention wherein $R^7$ is a carboxyl group and Z is a ketal derivative of —CO—CH=CH—. When $R^2$ in the compound of the formula (28) is a protective group of a phenolic hydroxyl group, the compound wherein $R^2$ is a hydrogen atom can be obtained by removing the protective group of a phenolic hydroxyl group.

A compound of the compounds of the formula (29) wherein $R^2$ is a hydrogen atom represents the same compound as the compound represented by the general formula (2) of the invention wherein $R^7$ is a carboxyl group and Z is a ketal derivative of —CO—CH$_2$CH$_2$—. When $R^2$ in the compound of the formula (29) is a protective group of a phenolic hydroxyl group, the compound wherein $R^2$ is a hydrogen atom can be obtained by removing the protective group of a phenolic hydroxyl group.

Of the compounds represented by the general formula (1) of the invention, a compound wherein $R^3$ is —CH$_2$OH and Z is —CHOH—CH=CH— (hereinafter referred to as a compound of the formula (30)) can be synthesized by reducing the ester and ketone of the compound of the formula (4) mentioned above into an alcohol.

Of the compounds represented by the general formula (1) of the invention, a compound wherein $R^3$ is —CH$_2$OH and Z is —CHOH-1,2-epoxy- (hereinafter referred to as a compound of the formula (31)) can be synthesized by epoxidizing the compound of the formula (30).

The following shows the conversion of the formula (4) into the formula (30) and the formula (31).

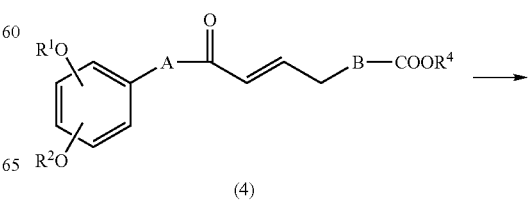

(4)

-continued

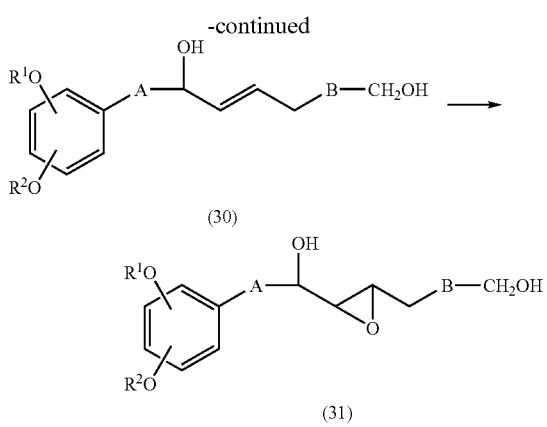

R¹, R², R⁴, A, and B in the formula (30) and the formula (31) are as defined in the formula (1).

The reaction conditions at the reduction reaction for the production of the compound of the formula (30) from the formula (4) vary depending on the kind of the structures of R¹, R², and R⁴ in the formula (4). For example, when the protective group of the carboxylic acid is an ethyl group, the compound of the formula (30) is obtained by using a metal-hydrogen complex compound or a metal hydride. As the metal-hydrogen complex compound, there may be mentioned lithium aluminum hydride, lithium tributoxyaluminum hydride, sodium bis(2-methoxyethoxy)aluminum hydride, and the like. Additionally, as the metal hydride, there may be diisobutylaluminum hydride and the like. In particular, the reducing agents preferably usable are lithium aluminum hydride and diisobutylaluminum hydride.

The amount of the above reducing agent to be used varies depending on the structures of R¹, R², and R⁴ in the formula (4) and the kind of the reducing agents but is preferably from 1 to 10 chemical equivalents, more preferably from 2 to 5 chemical equivalents relative to the compound of the formula (4).

The above reduction reaction is preferably carried out in the presence of a solvent and there may be used tetrahydrofuran, 1,4-dioxane, diethyl ether, 1,2-dimethoxyethane, diglyme, toluene, dichloromethane, and mixed solvents thereof.

Suitably, the reaction temperature at the above reduction reaction is preferably from −100° C. to 80° C., more preferably −78° C. to room temperature. The reaction time is suitably from several minutes to several hours. After completion of the reaction, the compound of the formula (30) can be obtained by a known purification method such as solvent extraction or column chromatography.

Of the compounds of the formula (30), a compound wherein R² is a hydrogen atom represents the same compound as the compound represented by the general formula (2) of the invention wherein R⁷ is —CH₂OH and Z is —CHOH—CH=CH—. When R² in the compound of the formula (30) is a protective group of a phenolic hydroxyl group, the compound wherein R² is a hydrogen atom can be obtained by removing the protective group of a phenolic hydroxyl group.

The epoxidizing agents to be used at the time when the compound of the formula (31) is produced are the same as the epoxidizing agents to be used at the time when the compound of the formula (12) is produced from the compound of the formula (11).

The solvents to be used at the time when the compound of the formula (31) is produced are the same as the solvents used at the time when the compound of the formula (12) is produced from the compound of the formula (11).

Suitably, the reaction temperature at the time when the compound of the formula (31) is produced is preferably from −100° C. to 80° C., more preferably −78° C. to room temperature. The reaction time is suitably from several tens minutes to several hours. After completion of the reaction, the compound of the formula (31) can be obtained by a known purification method such as solvent extraction or column chromatography.

Of the compounds of the formula (31), a compound wherein R² is a hydrogen atom represents the same compound as the compound represented by the general formula (2) of the invention wherein R⁷ is —CH₂OH and Z is —CHOH-1,2-epoxy-. When R² in the compound of the formula (31) is a protective group of a phenolic hydroxyl group, the compound wherein R² is a hydrogen atom can be obtained by removing the protective group of a phenolic hydroxyl group.

Of the compounds represented by the general formula (1) of the invention, a compound wherein R³ is —CH₂OH and Z is —CHOH—CH₂CHOH— (hereinafter referred to as a compound of the formula (32)) can be synthesized by reducing the compound of the formula (12).

The following shows the conversion from the formula (12) into the formula (32).

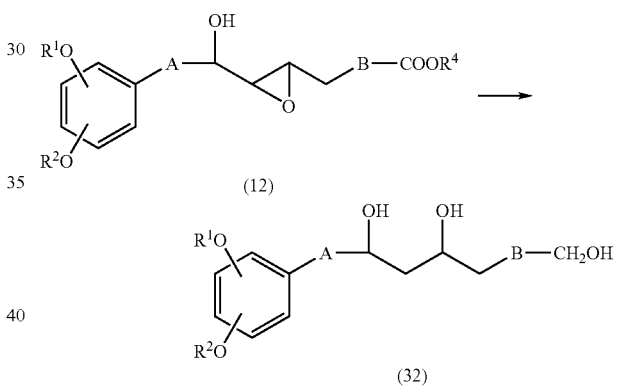

R¹, R², R⁴, A, and B in the formula (32) are as defined in the formula (1).

The reducing agents to be used at the time when the compound of the formula (32) is produced from the compound of the formula (12) are the same as the reducing agents used at the time when the compound of the formula (30) is produced from the compound of the formula (4), and are preferably lithium aluminum hydride and diisobutylaluminum hydride.

The solvents to be used at the time when the compound of the formula (32) is produced are the same as the solvents used at the time when the compound of the formula (30) is produced from the compound of the formula (4).

Suitably, the reaction temperature at the above reaction is preferably from −100° C. to 80° C., more preferably −78° C. to room temperature. The reaction time is suitably from several minutes to several hours. After completion of the reaction, the compound of the formula (32) can be obtained by a known purification method such as solvent extraction or column chromatography.

Of the compounds of the formula (32), a compound wherein R² is a hydrogen atom represents the same compound as the compound represented by the general formula (2) of the invention wherein $R^7$ is —CH$_2$OH and Z is —CHOH—CH$_2$CHOH—. When $R^2$ in the compound of the formula (32) is a protective group of a phenolic hydroxyl group, the compound wherein $R^2$ is a hydrogen atom can be obtained by removing the protective group of a phenolic hydroxyl group.

Of the compounds represented by the general formula (1) of the invention, a compound wherein $R^3$ is —CH$_2$OH and Z is —CO—CH$_2$CHOR$^5$— (hereinafter referred to as a compound of the formula (34)) can be synthesized by adding a lower alcohol to the compound represented by the formula (33) mentioned below (hereinafter referred to as a compound of the formula (33)) in the presence of a basic compound.

The following shows the conversion from the formula (33) into the formula (34).

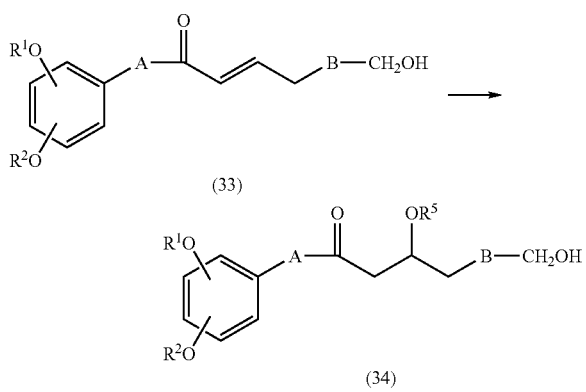

$R^1$, $R^2$, $R^5$, A, and B in the formula (34) are as defined in the formula (1).

The basic compounds to be used at the time when the compound of the formula (34) is produced from the compound of the formula (33) are the same as the basic compounds used at the time when the compound of the formula (17) is produced from the compound of the formula (4). Moreover, the lower alcohols to be used at the time when the compound of the formula (34) is produced are the same as the lower alcohols used at the time when the compound of the formula (17) is produced from the compound of the formula (4).

Suitably, the reaction temperature at the time when the compound of the formula (34) is produced is preferably from 0° C. to 150° C., more preferably room temperature to 100° C. The reaction time is suitably from several hours to several tens hours. After completion of the reaction, the compound of the formula (34) can be obtained by a known purification method such as solvent extraction or column chromatography.

Of the compounds of the formula (34), a compound wherein $R^2$ is a hydrogen atom represents the same compound as the compound represented by the general formula (2) of the invention wherein $R^7$ is —CH$_2$OH and Z is —CO—CH$_2$CHOR$^5$—. When $R^2$ in the compound of the formula (34) is a protective group of a phenolic hydroxyl group, the compound wherein $R^2$ is a hydrogen atom can be obtained by removing the protective group of a phenolic hydroxyl group.

Of the compounds represented by the general formula (1) of the invention, a compound wherein $R^3$ is —CH$_2$OH and Z is —CHOH—CH$_2$CHOR$^5$— (hereinafter referred to as a compound of the formula (35)) can be synthesized by reducing the ester or ketone of the compound of the formula (17) mentioned above into an alcohol.

The following shows the conversion from the formula (17) into the formula (35).

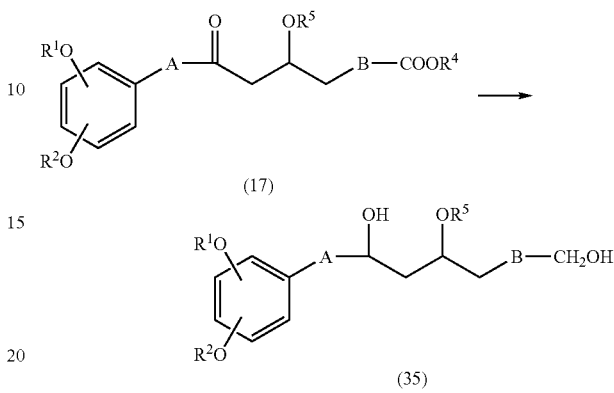

$R^1$, $R^2$, $R^4$, $R^5$, A, and B in the formula (35) are as defined in the formula (1).

The reducing agents to be used at the time when the compound of the formula (35) is produced from the compound of the formula (17) are the same as the reducing agents used at the time when the compound of the formula (30) is produced from the compound of the formula (4), and are preferably lithium aluminum hydride and diisobutylaluminum hydride.

The solvents to be used at the time when the compound of the formula (35) is produced are the same as the solvents used at the time when the compound of the formula (30) is produced from the compound of the formula (4).

Suitably, the reaction temperature at the time when the compound of the formula (35) is produced is preferably from −100° C. to 80° C., more preferably −78° C. to room temperature. The reaction time is suitably from several minutes to several hours. After completion of the reaction, the compound of the formula (35) can be obtained by a known purification method such as solvent extraction or column chromatography.

Of the compounds of the formula (35), a compound wherein $R^2$ is a hydrogen atom represents the same compound as the compound represented by the general formula (2) of the invention wherein $R^7$ is —CH$_2$OH and Z is —CHOH—CH$_2$CHOR$^5$—. When $R^2$ in the compound of the formula (35) is a protective group of a phenolic hydroxyl group, the compound wherein $R^2$ is a hydrogen atom can be obtained by removing the protective group of a phenolic hydroxyl group.

Of the compounds represented by the general formula (1) of the invention, a compound wherein $R^3$ is —CH$_2$OH and Z is a ketal derivative of —CO—CH═CH— (hereinafter referred to as a compound of the formula (36)) can be synthesized by reducing the ester of the compound of the formula (19) into an alcohol.

Furthermore, the compound of the formula (33) mentioned above can be synthesized by removing the ketal of the compound of the formula (36).

The following shows the conversion from the formula (19) into the formula (36) and the formula (33).

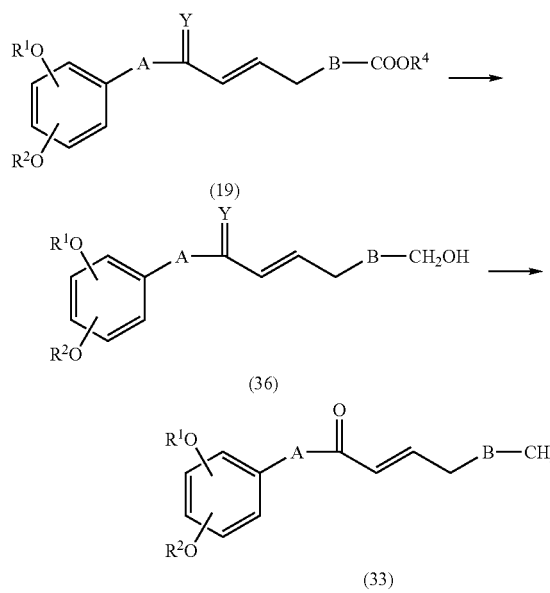

(19)

(36)

(33)

$R^1$, $R^2$, A, B and Y in the formula (33) and the formula (36) are as defined in the formula (1).

The reducing agents to be used at the time when the compound of the formula (36) is produced from the compound of the formula (19) are the same as the reducing agents used at the time when the compound of the formula (30) is produced from the compound of the formula (4), and are preferably lithium aluminum hydride and diisobutylaluminum hydride.

The solvents to be used at the time when the compound of the formula (36) is produced are the same as the solvents used at the time when the compound of the formula (30) is produced from the compound of the formula (4).

Suitably, the reaction temperature at the time when the compound of the formula (36) is produced is preferably from −100° C. to 80° C., more preferably −78° C. to room temperature. The reaction time is suitably from several minutes to several hours. After completion of the reaction, the compound of the formula (36) can be obtained by a known purification method such as solvent extraction or column chromatography.

Of the compounds of the formula (36), a compound wherein $R^2$ is a hydrogen atom represents the same compound as the compound represented by the general formula (2) of the invention wherein $R^7$ is —$CH_2OH$ and Z is a ketal derivative of —CO—CH=CH—. When $R^2$ in the compound of the formula (36) is a protective group of a phenolic hydroxyl group, the compound wherein $R^2$ is a hydrogen atom can be obtained by removing the protective group of a phenolic hydroxyl group.

The reaction for removing the ketal from the compound of the formula (36) can be carried out in accordance with known methods well known in the field of organic synthetic chemistry, e.g., methods described in T. W. Greene., "Protective Groups in Organic Synthesis", John Wiley & Sons, whereby the compound of the formula (33) can be obtained.

Of the compounds of the formula (33), a compound wherein $R^2$ is a hydrogen atom represents the same compound as the compound represented by the general formula (2) of the invention wherein $R^7$ is —$CH_2OH$ and Z is —CO—CH=CH—. When $R^2$ in the compound of the formula (33) is a protective group of a phenolic hydroxyl group, the compound wherein $R^2$ is a hydrogen atom can be obtained by removing the protective group of a phenolic hydroxyl group.

Of the compounds represented by the general formula (1) of the invention, a compound wherein $R^3$ is —$CH_2OH$ and Z is a ketal derivative of —CO—$CH_2CH_2$— (hereinafter referred to as a compound of the formula (37)) can be synthesized by reducing the ester of the compound of the formula (20) into an alcohol.

Furthermore, a compound represented by the formula (38) (hereinafter referred to as a compound of the formula (38)) can be synthesized by removing the ketal of the compound of the formula (37).

The following shows the conversion from the formula (20) into the formula (37) and the formula (38).

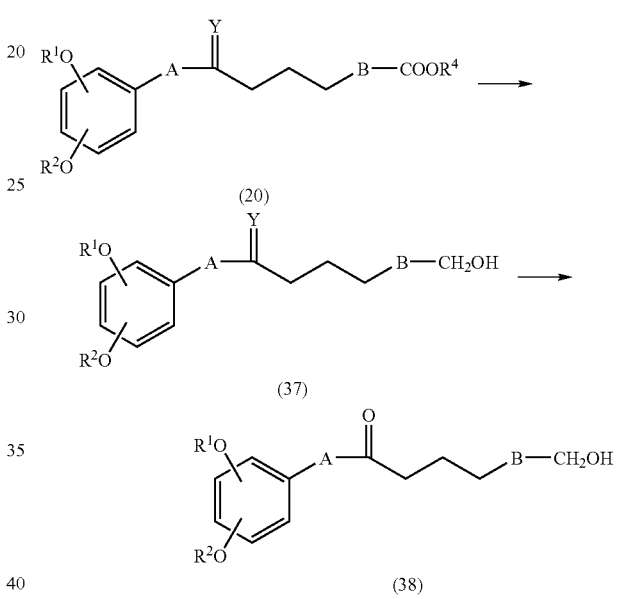

(20)

(37)

(38)

$R^1$, $R^2$, A, B, and Y in the formula (37) and the formula (38) are as defined in the formula (1).

The reducing agents to be used at the time when the compound of the formula (37) is produced from the compound of the formula (20) are the same as the reducing agents used at the time when the compound of the formula (30) is produced from the compound of the formula (4), and are preferably lithium aluminum hydride and diisobutylaluminum hydride.

The solvents to be used at the time when the compound of the formula (37) is produced are the same as the solvents used at the time when the compound of the formula (30) is produced from the compound of the formula (4).

Suitably, the reaction temperature at the time when the compound of the formula (37) is produced is preferably from −100° C. to 80° C., more preferably −78° C. to room temperature. The reaction time is suitably from several minutes to several hours. After completion of the reaction, the compound of the formula (37) can be obtained by a known purification method such as solvent extraction or column chromatography.

Of the compounds of the formula (37), a compound wherein $R^2$ is a hydrogen atom represents the same compound as the compound represented by the general formula (2) of the invention wherein $R^7$ is —$CH_2OH$ and Z is a ketal derivative of —CO—CH$_2$—CH$_2$—. When R$^2$ in the compound of the formula (37) is a protective group of a phenolic hydroxyl group, the compound wherein R$^2$ is a hydrogen atom can be obtained by removing the protective group of a phenolic hydroxyl group.

The reaction for removing the ketal from the compound of the formula (37) can be carried out in accordance with known methods well known in the field of organic synthetic chemistry, e.g., methods described in T. W. Greene., "Protective Groups in Organic Synthesis", John Wiley & Sons, whereby the compound of the formula (38) can be obtained.

Of the compounds of the formula (38), a compound wherein R$^2$ is a hydrogen atom represents the same compound as the compound represented by the general formula (2) of the invention wherein R$^7$ is —CH$_2$OH and Z is —CO—CH$_2$CH$_2$—. When R$^2$ in the compound of the formula (38) is a protective group of a phenolic hydroxyl group, the compound wherein R$^2$ is a hydrogen atom can be obtained by removing the protective group of a phenolic hydroxyl group.

A compound represented by the general formula (39) (hereinafter referred to as a compound of the formula (39)) can be synthesized by removing the protective group of the carboxyl group from the compound of the formula (13) of the invention.

Similarly, a compound represented by the general formula (40) (hereinafter referred to as a compound of the formula (40)) can be synthesized from the compound of the formula (15) of the invention by removing the protective group of the carboxyl group.

The following shows the conversion from the formula (13) into the formula (39) and the conversion from the formula (15) into the formula (40).

R$^1$, R$^2$, A, and B in the formula (39) and the formula (40) are as defined in the formula (1).

The reaction conditions to be used at the time when the compound of the formula (39) is produced from the compound of the formula (13) and the compound of the formula (40) is produced from the compound of the formula (15) are the same as the reaction conditions at the time when the compound of the formula (21) is produced from the compound of the formula (4).

The solvents to be used at the time when the compound of the formula (39) and the compound of the formula (40) are produced are the same as the solvents used at the time when the compound of the formula (21) is produced from the compound of the formula (4).

Suitably, the reaction temperature at the time when the compound of the formula (39) and the compound of the formula (40) are produced is preferably from −20° C. to 80° C., more preferably 0° C. to 50° C. When the reaction temperature is too low, the progress of the reaction is low in some cases and when the reaction temperature is too high, side reactions may proceed in some cases. The reaction time varies depending on conditions but is usually from several tens minutes to several hours. After completion of the reaction, the respective aimed compounds can be obtained by a known purification method such as solvent extraction or column chromatography.

Of the compounds of the formula (39), a compound wherein R$^2$ is a hydrogen atom represents the same compound as the compound represented by the general formula (2) of the invention wherein R$^7$ is a carboxyl group and Z is —CO—CH$_2$CH$_2$—. When R$^2$ in the compound of the formula (39) is a protective group of a phenolic hydroxyl group, the compound wherein R$^2$ is a hydrogen atom can be obtained by removing the protective group of a phenolic hydroxyl group.

Of the compounds of the formula (40), a compound wherein R$^2$ is a hydrogen atom represents the same compound as the compound represented by the general formula (2) of the invention wherein R$^7$ is a carboxyl group and Z is —CO—CH$_2$CHOH—. When R$^2$ in the compound of the formula (40) is a protective group of a phenolic hydroxyl group, the compound wherein R$^2$ is a hydrogen atom can be obtained by removing the protective group of a phenolic hydroxyl group.

By reducing the compounds of the formula (13) of the invention, a compounds represented by the formula (41) (hereinafter referred to as a compound of the formula (41)) can be synthesized.

The following shows the conversion from the formula (13) into the formula (41).

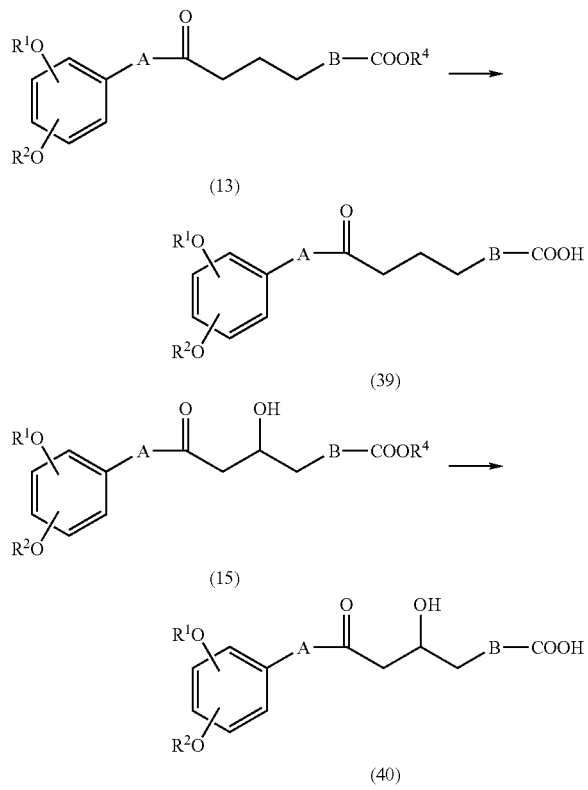

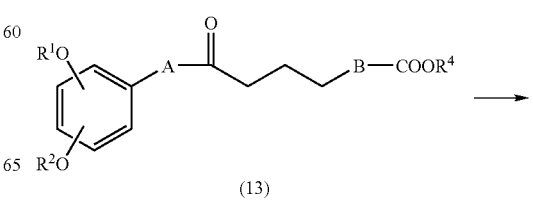

-continued

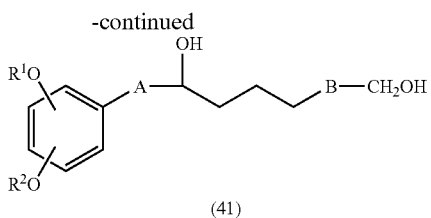

(41)

$R^1$, $R^2$, A, and B in the formula (41) are as defined in the formula (1).

The reducing agents to be used at the time when the compound of the formula (41) is produced from the compound of the formula (13) are the same as the reducing agents used at the time when the compound of the formula (30) is produced from the compound of the formula (4), and are preferably lithium aluminum hydride and diisobutylaluminum hydride.

The solvents to be used at the time when the compound of the formula (41) is produced are the same as the solvents used at the time when the compound of the formula (30) is produced from the compound of the formula (4).

Suitably, the reaction temperature at the time when the compound of the formula (41) is produced is preferably from −100° C. to 80° C., more preferably −78° C. to room temperature. The reaction time is suitably from several minutes to several hours. After completion of the reaction, the compound of the formula (41) can be obtained by a known purification method such as solvent extraction or column chromatography.

Of the compounds of the formula (41), a compound wherein $R^2$ is a hydrogen atom represents the same compound as the compound represented by the general formula (2) of the invention wherein $R^7$ is —CH$_2$OH and Z is —CHOH—CH$_2$CH$_2$—. When $R^2$ in the compound of the formula (41) is a protective group of a phenolic hydroxyl group, the compound wherein $R^2$ is a hydrogen atom can be obtained by removing the protective group of a phenolic hydroxyl group.

By adding water molecule to the compounds of the formula (33) of the invention, a compounds represented by the general formula (42) (hereinafter referred to as a compound of the formula (42)) can be obtained.

The following shows the conversion from the formula (33) into the formula (42).

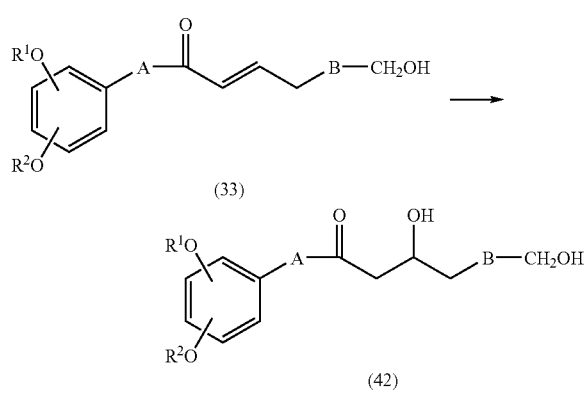

$R^1$, $R^2$, A, and B in the formula (42) are as defined in the formula (1).

The reaction conditions at the time when the compound of the formula (42) is produced from the compound of the formula (33) are the same as the reaction conditions used at the time when the compound of the formula (15) is produced from the compound of the formula (4).

The solvents to be used at the time when the compound of the formula (42) is produced are the same as the solvents used at the time when the compound of the formula (15) is produced from the compound of the formula (4).

Suitably, the reaction temperature at the time when the compound of the formula (42) is produced is preferably from 0° C. to 150° C., more preferably room temperature to 100° C. The reaction time is suitably from several hours to several tens hours. After completion of the reaction, the compound of the formula (42) can be obtained by a known method such as solvent extraction or column chromatography.

Of the compounds of the formula (42), a compound wherein $R^2$ is a hydrogen atom represents the same compound as the compound represented by the general formula (2) of the invention wherein $R^7$ is —CH$_2$OH and Z is —CO—CH$_2$CHOH—. When $R^2$ in the compound of the formula (42) is a protective group of a phenolic hydroxyl group, the compound wherein $R^2$ is a hydrogen atom can be obtained by removing the protective group of a phenolic hydroxyl group.

Among the compounds represented by the general formulae (1) and (2) of the invention, there are compounds having one or two asymmetric carbons. They are usually obtained as racemic mixtures, but it is possible to separate and use only one optical isomer by a method of synthesizing only one optical isomer through asymmetric synthesis or a method of high performance liquid chromatography using an optically active column, or the like, if necessary.

The compounds represented by the general formula (1) and the compounds represented by the general formula (2) according to the invention can inhibit activity of tyrosinase which is an oxidase of L-tyrosine. Moreover, the compounds represented by the general formula (1) and the compounds represented by the general formula (2) are considered to have also an action of scavenging hydroxy radicals and an activity of suppressing formation of lipid peroxide. In this connection, in the case that $R^1$ is a lower alkyl group or a protective group of a phenolic hydroxyl group and $R^2$ is a protective group of a phenolic hydroxyl group in the compounds represented by the formula (1), these activities do not exhibited sometimes in vitro. For such a compounds, these activities can be expected in vivo.

From this fact, it is predicted that suppression of the formation of melanin pigment and suppression of pigmentation onto skin and the like are possible. All of these compounds can be used with mixing into formulations of foods, medicines, quasi-drugs, cosmetics, etc. In the case that they are used as skin external preparations for the purpose of preventing and improving spots and freckles, it is preferable to mix them into toilet water, liquid cosmetics, milky lotions, creams, packs, and the like.

Moreover, since the compounds represented by the general formula (2) exhibit an effect of inhibiting hyaluronic acid-degrading enzyme and further an effect of scavenging free radicals and an effect of suppressing formation of lipid peroxide, they can be suitably used with mixing into formulations of foods, medicines, quasi-drugs, cosmetics, etc.

The compounds 6, 12, 17, 22, 26, 27, 28, 29, 30, 31, 32 and/or 33 can be used as tyrosinase activity inhibitors, hyaluronic acid-degrading enzyme inhibitors, antioxidants, hydroxy radical scavengers, and/or lipid peroxide formation suppressors.

The compounds 7, 8, 13, 18, 19, 23, 34, 35, 36, 37, 38, 39, 40, 41, 42, 43, 44, 45, 46, 47, and/or 48 can be used as tyrosinase activity inhibitors, hyaluronic acid-degrading enzyme inhibitors, antioxidants, hydroxy radical scavengers, and/or lipid peroxide formation suppressors.

EXAMPLES

The following will describe the invention in detail with reference to Examples but the invention is not limited to these Examples. In this connection, Ts represents a p-toluenesulfonyl group.

Synthetic Example 1

As a starting material for synthesizing the compound of the formula (4) of the invention, the compound 5 was prepared via the compound 2 and the compound 3 using the compound 1 as a starting material.

In this connection, the compound 1 corresponds to the compound of the formula (8), the compound 2 to the compound of the formula (10), the compound 3 to the compound of the formula (5), the compound 4 to the compound of the formula (6), and the compound 5 to the compound of the formula (7).

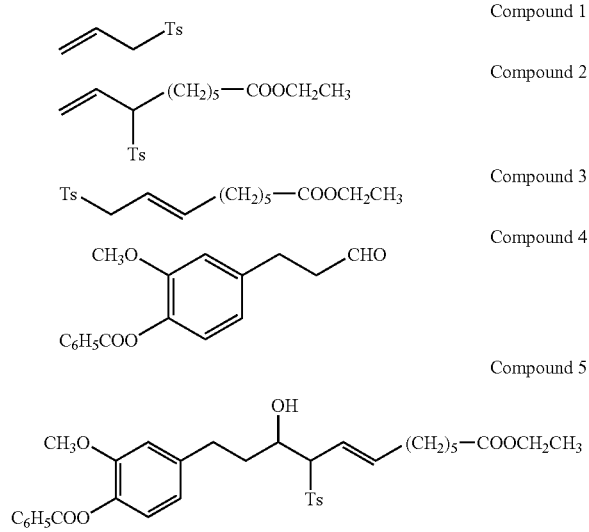

First, conversion of ethyl 6-bromohexanoate into ethyl 6-iodohexanoate was carried out. Namely, 39.1 g (175 mmol) of ethyl 6-bromohexanoate was dissolved in 250 ml of acetone, and 29.1 g (175 mmol) of potassium iodide was added thereto, followed by heating under reflux over a period of 20 hours. Then, after the reaction solution was allowed to cool to room temperature, the solvent was removed by distillation and the residue was extracted with 150 ml of ethyl acetate. The resulting organic layer was washed with 50 ml of distilled water and then dried over anhydrous magnesium sulfate. After drying, 47.4 g of a crude product was obtained by removing the solvent by distillation and drying under reduced pressure. As a result of $^1$H-NMR analysis thereof, it was found that the crude product contained ethyl 6-iodohexanoate in a molar fraction of about 90%. The crude product was used in the following step without further purification.

Next, 30.5 g (155 mmol) of the compound 1 was dissolved in 450 ml of tetrahydrofuran, and the resulting solution was cooled to −78° C. with dry ice/acetone. To the resulting solution was dropwise added 100 ml (156 mmol) of 1.56 M n-butyllithium/n-hexane solution. After the resulting mixture was stirred at the same temperature for 45 minutes, a solution of the crude product of ethyl 6-iodohexanoate prepared in the above, which had been dissolved in 50 ml of tetrahydrofuran, was dropwise added to the mixture. After dropwise addition, the resulting mixture was stirred at the same temperature for 10 minutes and then, the temperature was gradually elevated. When the temperature of the reaction solution reached −10° C., 50 ml of 5% citric acid aqueous solution was added to terminate the reaction. To the reaction mixture were added 100 ml of 10% sodium thiosulfate aqueous solution, 150 ml of saturated sodium chloride aqueous solution, and 50 ml of ethyl acetate, followed by partitioning. The organic layer was separated and the aqueous layer was extracted in 50 ml of ethyl acetate. The combined organic layer was dried over anhydrous magnesium sulfate. After drying, the solvent was removed by distillation and purification by silica gel column chromatography was carried out to obtain 49.5 g (yield 94%) of a pale yellow, liquid compound having a low viscosity.

The chemical shift values of the product on $^1$H-NMR spectrum as measured in deuterochloroform were as follows: 1.20-1.70 (9H, m), 2.03-2.15 (2H, m), 2.23-2.35 (2H, m), 2.44 (3H, s), 3.43-3.55 (1H, m), 4.11 (2H, q), 5.04 (1H, d), 5.25-5.35 (1H, m), 5.53-5.68 (1H, m), 7.32 (2H, d), 7.70 (2H, d).

The wave numbers (cm$^{-1}$) with absorption on IR absorption spectrum (KBr pellet method) were as follows: 2930, 2860, 1730, 1600, 1300, 1290, 1180, 1140, 940, 670.

The results of elemental analysis were as follows: carbon 64.09% and hydrogen 7.87%.

Based on the above analysis, it was confirmed that the obtained compound was the compound 2.

Next, Conversion From the Compound 2 to the Compound 3 was Carried Out.

Into 360 ml of tetrahydrofuran and 120 ml of methanol was dissolved 49.5 g (146 mmol) of the compound 2, and 3.38 g (2.92 mmol) of tetrakistriphenylphosphine palladium was added. The reaction solution was heated under reflux over a period of 16 hours. Then, after the reaction solution was allowed to cool to room temperature, the solvent was removed by distillation and purification by silica gel chromatography was carried out to obtain 47.1 g (95%) of a pale brown, liquid compound having a low viscosity. As a result of $^1$H-NMR analysis, IR absorption spectrum analysis, and elemental analysis shown below, it was confirmed that the product contained the compound 3 in a molar fraction of 73% and the remaining 27% was a geometrical isomer wherein the carbon-carbon double bond in the compound 3 was arranged in a cis-form.

The chemical shift values of the compound 3 on $^1$H-NMR spectrum as measured in deuterochloroform were as follows: 1.20-1.33 (7H, m), 1.50-1.60 (2H, m), 1.99 (2H, t), 2.20-2.30 (2H, m), 2.45 (3H, s), 3.73 (2H, d), 4.08-4.15 (2H, q), 5.35-5.55 (2H, m), 7.34 (2H, d), 7.72 (2H, d).

The wave numbers (cm$^{-1}$) with absorption on IR absorption spectrum (KBr pellet method) were as follows: 2930, 2860, 1730, 1600, 1320, 1150, 1090, 1030, 820, 740.

The results of elemental analysis were as follows: carbon 64.03% and hydrogen 7.57%.

Next, Conversion From the Compound 3 to the Compound 5 was Carried Out.

A solution of 8.75 g (25.8 mmol) of the compound 3 dissolved in 75 ml of tetrahydrofuran was cooled to −78° C. with dry ice/acetone. To the solution was dropwise added 13.0 ml (26.0 mmol) of 2.0 M lithium diisopropylamide/heptane-tetrahydrofuran-ethylbenzene solution. After the resulting mixture was stirred at the same temperature for 60 minutes, a solution of 7.34 g (25.8 mmol) of the compound 4 dissolved in 30 ml of tetrahydrofuran was dropwise added thereto. After dropwise addition, the resulting mixture was stirred at the same temperature for 30 minutes and then, the temperature was gradually elevated. When the temperature of the reaction solution reached −30° C., a solution obtained by dissolving 3.0 g of citric acid in 10 ml of methanol was added to terminate the reaction. To the reaction mixture were added 30 ml of distilled water, 50 ml of saturated sodium chloride aqueous solution, and 50 ml of ethyl acetate, followed by partitioning. The organic layer was separated and the aqueous layer was extracted with 50 ml of ethyl acetate. The combined organic layer was dried over anhydrous magnesium sulfate. The solvent was removed by distillation and purification by silica gel column chromatography was carried out to obtain 6.15 g (yield 38%) of a pale yellow, liquid compound having a medium viscosity.

The chemical shift values of the product on $^1$H-NMR spectrum as measured in deuterochloroform were as follows: 1.25 (3H, t), 1.44-2.04 (10H, m), 2.15-2.29 (2H, m), 2.45 (3H, s), 2.57-3.00 (2H, m), 3.12-4.62 (8H, m), 4.95-5.83 (2H, m), 6.71-6.88 (2H, m), 6.97-7.06 (1H, m), 7.34 (2H, d), 7.45-7.54 (2H, m), 7.58-7.77 (3H, m), 8.20 (2H, d).

The wave numbers (cm$^{-1}$) with absorption on IR absorption spectrum (KBr pellet method) were as follows: 3510, 2940, 2860, 1740, 1600, 1510, 1290, 1270, 1200, 1140, 1061, 1030, 710.

The results of elemental analysis were as follows: carbon 67.27% and hydrogen 6.95%.

Based on the above analysis, it was confirmed that the obtained compound was the compound 5.

Example 1

Starting from the compound 5 obtained in the above Synthetic Example 1, the compound 6 of the invention was prepared.

Compound 6

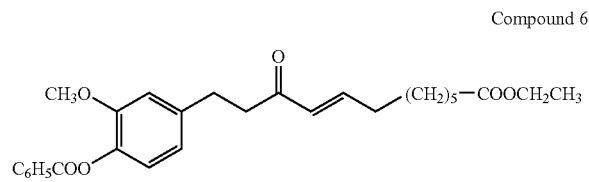

To a solution of 5.00 g (8.03 mmol) of the compound 5 dissolved in 120 g of 1,2-dichloroethane, 40 g of isopropyl alcohol, and 40 g of glycerin were added 3.40 ml (24.4 mmol) of triethylamine, 105 mg (0.400 mmol) of triphenylphosphine, and 462 mg (0.400 mmol) of tetrakistriphenylphosphine palladium, followed by stirring at a bath temperature of 100° C. for 16 hours. After cooling and concentration, 100 ml of distilled water, 50 ml of saturated sodium chloride aqueous solution, and 50 ml of ethyl acetate were added thereto, followed by partitioning. The organic layer was separated and washed with 30 ml of saturated sodium chloride aqueous solution. The combined aqueous layer was extracted with 30 ml of ethyl acetate. The combined organic layer was dried over anhydrous magnesium sulfate. The solvent was removed by distillation and purification by silica gel column chromatography was carried out to obtain 1.45 g (yield 39%) of a pale yellow, liquid compound having a medium viscosity.

The chemical shift values of the product on $^1$H-NMR spectrum as measured in deuterochloroform were as follows: 1.25 (3H, t), 1.30-1.53 (6H, m), 1.57-1.67 (2H, m), 2.16-2.32 (4H, m), 2.84-3.00 (4H, m), 3.80 (3H, s), 4.12 (2H, q), 6.11 (1H, d), 6.77-6.88 (3H, m), 7.05 (1H, d), 7.46-7.53 (2H, m), 7.59-7.67 (1H, m), 8.21 (2H, d).

The wave numbers (cm$^{-1}$) with absorption on IR absorption spectrum (KBr pellet method) were as follows: 2930, 2860, 1730, 1700, 1670, 1630, 1600, 1510, 1270, 1200, 1150, 1060, 1030, 710.

The results of elemental analysis were as follows: carbon 71.81% and hydrogen 7.25%.

Based on the above analysis, it was confirmed that the obtained compound was the compound 6.

Example 2

Starting from the compound 6 obtained in the above Synthetic Example 1, the compound 7 of the invention was prepared.

Compound 7

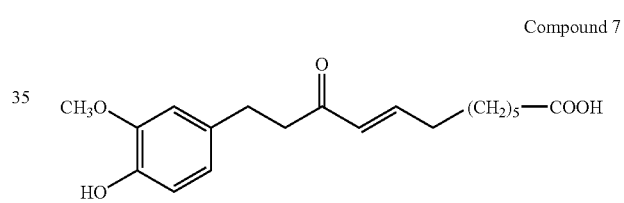

To a solution of 467 mg (1.00 mmol) of the compound 6 dissolved in 7 ml of 1,4-dioxane was added 3 ml of 1N sodium hydroxide aqueous solution, followed by stirring. After 4 hours of stirring, 3 ml of 1N hydrochloric acid was added to neutralize the mixture. To the reaction solution was added 30 ml of saturated sodium chloride aqueous solution and extraction with 10 ml of chloroform was repeated three times. The combined organic layer was dried over anhydrous magnesium sulfate and then concentrated. The obtained residue was purified by silica gel column chromatography to obtain 174 mg (52%) of a colorless crystalline compound.

The chemical shift values of the product on $^1$H-NMR spectrum as measured in deuterochloroform were as follows: 1.23-1.50 (6H, m), 1.57-1.69 (2H, m), 2.19 (2H, q), 2.34 (2H, t), 2.79-2.90 (4H, m), 3.87 (3H, s), 6.08 (1H, d), 6.64-6.85 (4H, m).

The wave numbers (cm$^{-1}$) with absorption on IR absorption spectrum (KBr pellet method) were as follows: 3530, 2930, 2850, 1700, 1660, 1640, 1520, 1280, 1230, 1030.

The results of elemental analysis were as follows: carbon 68.48% and hydrogen 8.11%.

Based on the above analysis, it was confirmed that the obtained compound was the compound 7.

Example 3

Starting from the compound 6 obtained in Example 1, a mixture of the compound 7 and the compound 8 of the invention was prepared.

Compound 8

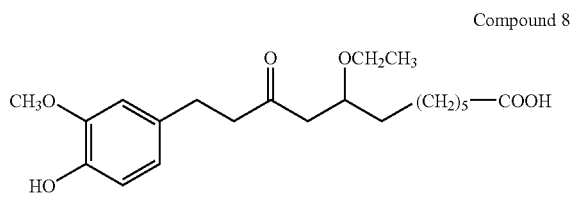

To a solution of 467 mg (1.00 mmol) of the compound 6 dissolved in 7 ml of ethanol was added 3 ml of 1N sodium hydroxide aqueous solution. After 3 hours of stirring, 3 ml of 1N hydrochloric acid was added to terminate the reaction. To the reaction solution was added 30 ml of saturated sodium chloride aqueous solution and extraction with 10 ml of chloroform was repeated three times. The combined organic layer was dried over anhydrous magnesium sulfate and then concentrated. The obtained residue was purified by silica gel column chromatography to obtain 237 mg of a pale yellow, liquid compound having a medium viscosity.

As a result of analyzing $^1$H-NMR spectrum as measured in deuterochloroform, it was confirmed that the product was a mixture of the compound 7 and the compound 8 wherein ethanol used as the solvent was added to the double bond of the compound 7 (existing molar ratio of the compound 7 to the compound 8 was 35:65). Incidentally, the chemical shift value of the ethoxy group in the compound 8 was 1.12 (3H, t) and 3.35-3.50 (2H, m) and the chemical shift value of CH to which the ethoxy group was bonded was 3.68-3.78 (1H, m).

Synthetic Example 2

As a starting material for obtaining the compound of the formula (4), starting from the compound 1 as in Synthetic Example 1, the compound 11 was prepared via the compound 9 and the compound 10.

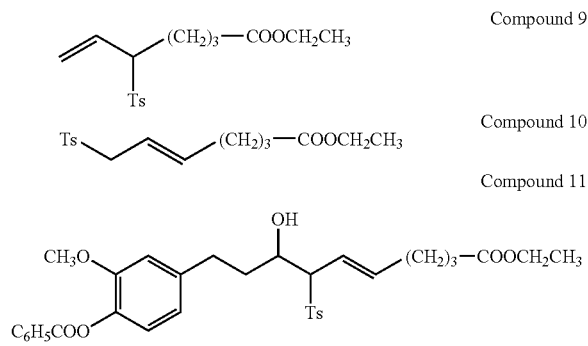

Compound 9

Compound 10

Compound 11

First, conversion of ethyl 4-bromobutyrate into ethyl 4-iodobutyrate was carried out.

Into 250 ml of acetone was dissolved 34.2 g (175 mmol) of ethyl 4-bromobutyrate, and then 29.1 g (175 mmol) of potassium iodide was added thereto, followed by heating under reflux over a period of 20 hours. Then, after the reaction solution was allowed to cool to room temperature, the solvent was removed by distillation and the residue was extracted with 150 ml of ethyl acetate. The resulting organic layer was washed with 50 ml of distilled water and then dried over anhydrous magnesium sulfate. Then, 43.2 g of a crude product was obtained by removing the solvent by distillation and drying under reduced pressure. As a result of $^1$H-NMR analysis, it was found that the crude product contained ethyl 4-iodobutyrate in a molar fraction of 92%. The crude product was used in the following step as it was.

Next, 30.5 g (155 mmol) of the compound 1 was dissolved in 450 ml of tetrahydrofuran, and the resulting solution was cooled to −78° C. with dry ice/acetone. To the resulting solution was dropwise added 100 ml (156 mmol) of 1.56 M n-butyllithium/n-hexane solution. After the resulting mixture was stirred at the same temperature for 45 minutes, a solution of the crude product of ethyl 4-iodobutyrate, which had been prepared as above and dissolved in 50 ml of tetrahydrofuran, was dropwise added to the mixture. After dropwise addition, the resulting mixture was stirred at the same temperature for 10 minutes and then, the temperature was gradually elevated. When the temperature of the reaction solution reached −10° C., 50 ml of 5% citric acid aqueous solution was added to terminate the reaction. To the reaction mixture were added 100 ml of 10% sodium thiosulfate aqueous solution, 150 ml of saturated sodium chloride aqueous solution, and 50 ml of ethyl acetate, followed by partitioning. The organic layer was separated and the aqueous layer was extracted in 50 ml of ethyl acetate. The combined organic layer was dried over anhydrous magnesium sulfate. The solvent was removed by distillation and purification by silica gel column chromatography was carried out to obtain 46.0 g (yield 96%) of a pale yellow, liquid compound having a low viscosity.

The chemical shift values of the product on $^1$H-NMR spectrum as measured in deuterochloroform were as follows: 1.23 (3H, t), 1.52-1.63 (1H, m), 1.65-1.80 (2H, m), 2.07-2.15 (1H, m), 2.25-2.37 (2H, m), 2.44 (3H, s), 3.45-3.55 (1H, m), 4.10 (2H, q), 5.08 (1H, d), 5.31 (1H, d), 5.57-5.66 (1H, m), 7.32 (2H, d), 7.70 (2H, d).

The wave numbers (cm$^{-1}$) with absorption on IR absorption spectrum (KBr pellet method) were as follows: 2980, 2930, 1730, 1600, 1300, 1290, 1140, 1090, 820, 670.

The results of elemental analysis were as follows: carbon 61.73% and hydrogen 6.92%.

Based on the above analysis, it was confirmed that the obtained compound was the compound 9.

Next, Conversion From the Compound 9 to the Compound 10 was Carried Out.

Into 360 ml of tetrahydrofuran and 120 ml of methanol was dissolved 46.0 g (148 mmol) of the compound 9, and 3.42 g (2.96 mmol) of tetrakistriphenylphosphine palladium was added. The reaction solution was heated under reflux over a period of 16 hours. Then, after the reaction solution was allowed to cool to room temperature, the solvent was removed by distillation and purification by silica gel chromatography was carried out to obtain 41.0 g (89%) of a pale brown, liquid compound having a low viscosity. As a result of $^1$H-NMR analysis, IR absorption spectrum analysis, and elemental analysis shown below, it was confirmed that the product contained the compound 10 in a molar fraction of 81% and the remaining 19% was a geometrical isomer wherein the carbon-carbon double bond in the compound 10 was arranged in a cis-form.

The chemical shift values of the compound 10 on $^1$H-NMR spectrum as measured in deuterochloroform were as follows: 1.25 (3H, t), 1.57-1.65 (2H, m), 2.03-2.10 (2H, m), 2.20 (2H, t), 2.44 (3H, s), 3.73 (2H, d), 4.12 (2H, q), 5.37-5.55 (2H, m), 7.33 (2H, d), 7.73 (2H, d).

The wave numbers (cm$^{-1}$) with absorption on IR absorption spectrum (KBr pellet method) were as follows: 2980, 2930, 1730, 1600, 1320, 1300, 1150, 1090, 820, 740.

The results of elemental analysis were as follows: carbon 61.81% and hydrogen 7.01%.

The compound 11 was prepared from the compound 10.

A solution of 6.63 g (21.4 mmol) of the compound 10 dissolved in 65 ml of tetrahydrofuran was cooled to –78° C. with dry ice/acetone. To the solution was dropwise added 11.0 ml (22.0 mmol) of 2.0 M lithium diisopropylamide/heptane-tetrahydrofuran-ethylbenzene solution. After the resulting mixture was stirred at the same temperature for 60 minutes, a solution of 6.09 g (21.4 mmol) of the compound 4 dissolved in 25 ml of tetrahydrofuran was dropwise added thereto. After dropwise addition, the resulting mixture was stirred at the same temperature for 30 minutes and then, the temperature was gradually elevated. When the temperature of the reaction solution reached –20° C., a solution obtained by dissolving 3.0 g of citric acid in 10 ml of methanol was added to terminate the reaction. To the reaction mixture were added 30 ml of distilled water, 50 ml of saturated sodium chloride aqueous solution, and 50 ml of ethyl acetate, followed by partitioning. The organic layer was separated and the aqueous layer was extracted with 50 ml of ethyl acetate. The combined organic layer was dried over anhydrous magnesium sulfate. The solvent was removed by distillation and purification by silica gel column chromatography was carried out to obtain 4.33 g (yield 34%) of a pale yellow, liquid compound having a medium viscosity.

The chemical shift values of the product on $^1$H-NMR spectrum as measured in deuterochloroform were as follows: 1.24 (3H, t), 1.38-2.50 (11H, m), 2.59-3.00 (2H, m), 3.15-4.58 (8H, m), 5.08-5.86 (2H, m), 6.69-6.91 (2H, m), 7.00-7.12 (1H, m), 7.28-7.38 (2H, m), 7.45-7.55 (2H, m), 7.58-7.79 (3H, m), 8.21 (2H, d).

The wave numbers (cm$^{-1}$) with absorption on IR absorption spectrum (KBr pellet method) were as follows: 3510, 2940, 1730, 1600, 1510, 1290, 1270, 1150, 1060, 710.

The results of elemental analysis were as follows: carbon 66.53% and hydrogen 6.58%.

Based on the above analysis, it was confirmed that the obtained compound was the compound 11.

Example 4

Starting from the compound 11 obtained in the above Synthetic Example 2, the compound 12 of the invention was prepared.

Compound 12

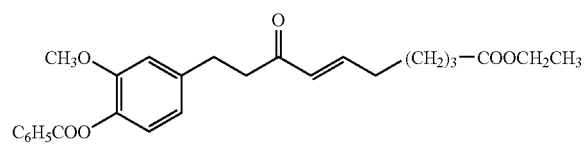

To a solution of 3.57 g (6.00 mmol) of the compound 11 dissolved in 90 g of 1,2-dichloroethane, 30 g of isopropyl alcohol, and 30 g of glycerin were added 2.50 ml (17.9 mmol) of triethylamine, 78.7 mg (0.300 mmol) of triphenylphosphine, and 347 mg (0.300 mmol) of tetrakistriphenylphosphine palladium, followed by stirring at a bath temperature of 100° C. for 16 hours. After cooling and concentration, 80 ml of distilled water, 40 ml of saturated sodium chloride aqueous solution, and 40 ml of ethyl acetate were added thereto, followed by partitioning. The organic layer was separated and washed with 25 ml of saturated sodium chloride aqueous solution. The combined aqueous layer was extracted with 25 ml of ethyl acetate. The combined organic layer was dried over anhydrous magnesium sulfate. The solvent was removed by distillation and purification by silica gel column chromatography was carried out to obtain 613 mg (yield 23%) of a pale yellow, liquid compound having a medium viscosity.

The chemical shift values of the product on $^1$H-NMR spectrum as measured in deuterochloroform were as follows: 1.25 (3H, t), 1.46-1.56 (2H, m), 1.61-1.72 (2H, m), 2.21-2.35 (4H, m), 2.86-3.00 (4H, m), 3.80 (3H, s), 4.13 (2H, q), 6.12 (1H, d), 6.77-6.87 (3H, m), 7.03-7.08 (1H, d), 7.47-7.54 (2H, m), 7.59-7.66 (1H, m), 8.21 (2H, d).

The wave numbers (cm$^{-1}$) with absorption on IR absorption spectrum (KBr pellet method) were as follows: 2940, 1740, 1670, 1630, 1600, 1510, 1270, 1200, 1150, 1060, 710.

The results of elemental analysis were as follows: carbon 70.91% and hydrogen 7.17%.

Based on the above analysis, it was confirmed that the obtained compound was the compound 12.

Example 5

Starting from the compound 12 obtained in the above Example 4, the compound 13 of the invention was prepared.

Compound 13

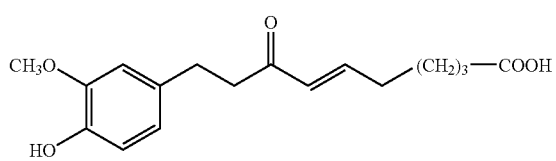

To a solution of 439 mg (1.00 mmol) of the compound 12 dissolved in 7 ml of 1,4-dioxane was added 3 ml of 1N sodium hydroxide aqueous solution, followed by stirring. After 4 hours of stirring, 3 ml of 1N hydrochloric acid was added to neutralize the mixture. To the reaction solution was added 30 ml of saturated sodium chloride aqueous solution and extraction with 10 ml of chloroform was repeated three times. The combined organic layer was dried over anhydrous magnesium sulfate and then concentrated. The obtained residue was purified by silica gel column chromatography to obtain 90.0 mg (29%) of a pale yellow, liquid compound having a medium viscosity.

The chemical shift values of the product on $^1$H-NMR spectrum as measured in deuterochloroform were as follows: 1.46-1.56 (2H, m), 1.60-1.72 (2H, m), 2.23 (2H, q), 2.38 (2H, t), 2.79-2.91 (4H, m), 3.86 (3H, s), 6.10 (1H, d), 6.64-6.85 (4H, m).

The wave numbers (cm$^{-1}$) with absorption on IR absorption spectrum (KBr pellet method) were as follows: 3400, 2940, 1710, 1660, 1630, 1520, 1270, 1240, 1150, 1030, 820, 720.

The results of elemental analysis were as follows: carbon 66.90% and hydrogen 7.11%.

Based on the above analysis, it was confirmed that the obtained compound was the compound 13.

Synthetic Example 3

As a starting material for obtaining the compound of the formula (4) of the invention, starting from the compound 1 as in Synthetic Example 1, the compound 16 was prepared via the compound 14 and the compound 15.

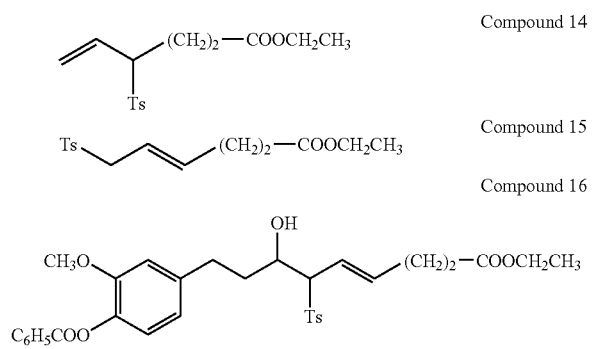

First, conversion from the compound 1 to the compound 14 was carried out.

A solution of 4.91 g (25.0 mmol) of the compound 1 and 656 mg (2.50 mmol) of triphenylphosphine dissolved in 80 ml of toluene was cooled to −78° C. with dry ice/acetone. To the solution was dropwise added 13.0 ml (26.0 mmol) of 2.0 M lithium diisopropylamide/heptane-tetrahydrofuran-ethylbenzene solution. After the resulting mixture was stirred at the same temperature for 30 minutes, a solution of 3.00 ml (27.7 mmol) of the ethyl acrylate dissolved in 15 ml of toluene was dropwise added thereto. After dropwise addition, the resulting mixture was stirred at the same temperature for 30 minutes, a solution obtained by dissolving 3.0 g of citric acid in 10 ml of methanol was added to terminate the reaction. To the reaction mixture were added 60 ml of saturated sodium chloride aqueous solution and 50 ml of ethyl acetate, followed by partitioning. The organic layer was separated and the aqueous layer was extracted with 20 ml of ethyl acetate. The combined organic layer was dried over anhydrous magnesium sulfate. The solvent was removed by distillation and purification by silica gel column chromatography was carried out to obtain 2.99 g (yield 40%) of a pale yellow, liquid compound having a low viscosity.

The chemical shift values of the product on $^1$H-NMR spectrum as measured in deuterochloroform were as follows: 1.23 (3H, t), 1.80-2.00 (1H, m), 2.30-2.49 (6H, m), 3.64 (1H, dt), 4.10 (2H, d), 5.10 (1H, m), 5.33 (1H, d), 5.56-5.68 (1H, m), 7.33 (2H, d), 7.71 (2H, d).

The wave numbers (cm$^{-1}$) with absorption on IR absorption spectrum (KBr pellet method) were as follows: 2980, 1730, 1600, 1380, 1290, 1150, 1090, 940, 820, 670.

The results of elemental analysis were as follows: carbon 60.97% and hydrogen 6.75%.

Based on the above analysis, it was confirmed that the obtained compound was the compound 14.

Next, Conversion From the Compound 14 to the Compound 15 was Carried Out.

Into 36 ml of tetrahydrofuran and 12 ml of methanol was dissolved 4.75 g (16.0 mmol) of the compound 14, and 277 mg (0.240 mmol) of tetrakistriphenylphosphine palladium was added. The reaction solution was heated under reflux over a period of 6 hours. Then, after the reaction solution was allowed to cool to room temperature, the solvent was removed by distillation and purification by silica gel chromatography was carried out to obtain 3.64 g (77%) of a pale brown, liquid compound having a low viscosity. As a result of $^1$H-NMR analysis, IR absorption spectrum analysis, and elemental analysis shown below, it was confirmed that the product contained the compound 15 in a molar fraction of 83% and the remaining 17% was a geometrical isomer wherein the carbon-carbon double bond in the compound 15 was arranged in a cis-form.

The chemical shift values of the compound 15 on $^1$H-NMR spectrum as measured in deuterochloroform were as follows: 1.25 (3H, t), 2.22-2.38 (4H, m), 2.45 (3H, s), 3.73 (2H, d), 4.12 (2H, q), 5.40-5.59 (2H, m), 7.34 (2H, d), 7.72 (2H, d).

The wave numbers (cm$^{-1}$) with absorption on IR absorption spectrum (KBr pellet method) were as follows: 2980, 2930, 1730, 1600, 1320, 1300, 1180, 1150, 1090, 820, 740.

The results of elemental analysis were as follows: carbon 60.54% and hydrogen 7.67%.

Next, Conversion From the Compound 15 to the Compound 16 was Carried Out.

Namely, a solution of 3.64 g (12.3 mmol) of the compound 15 dissolved in 50 ml of tetrahydrofuran was cooled to −78° C. with dry ice/acetone. To the solution was dropwise added 6.80 ml (13.6 mmol) of 2.0 M lithium diisopropylamide/heptane-tetrahydrofuran-ethylbenzene solution. After the resulting mixture was stirred at the same temperature for 60 minutes, a solution of 3.85 g (13.5 mmol) of the compound 4 dissolved in 20 ml of tetrahydrofuran was dropwise added thereto. After dropwise addition, the resulting mixture was stirred at the same temperature for 30 minutes and then, the temperature was gradually elevated. When the temperature of the reaction solution reached −15° C., a solution obtained by dissolving 1.0 g of citric acid in 5 ml of methanol was added to terminate the reaction. To the reaction mixture were added 30 ml of saturated sodium chloride aqueous solution and 20 ml of ethyl acetate, followed by partitioning. The organic layer was separated and the aqueous layer was extracted with 20 ml of ethyl acetate. The combined organic layer was dried over anhydrous magnesium sulfate. The solvent was removed by distillation and purification by silica gel column chromatography was carried out to obtain 2.39 g (yield 33%) of a pale yellow, liquid compound having a medium viscosity.

The chemical shift values of the product on $^1$H-NMR spectrum as measured in deuterochloroform were as follows: 1.18-1.32 (3H, m), 1.53-2.38 (6H, m), 2.46 (3H, s), 2.56-3.03 (2H, m), 3.18-4.59 (8H, m), 4.90-5.80 (2H, m), 6.72-6.80 (2H, m), 6.97-7.09 (1H, m), 7.30-7.39 (2H, m), 7.40-7.56 (2H, m), 7.61-7.73 (3H, m), 8.21 (2H, d).

The wave numbers (cm$^{-1}$) with absorption on IR absorption spectrum (KBr pellet method) were as follows: 3450, 2940, 1740, 1600, 1510, 1270, 1200, 1150, 1060, 1030, 710.

The results of elemental analysis were as follows: carbon 65.93% and hydrogen 6.13%.

Based on the above analysis, it was confirmed that the obtained compound was the compound 16.

Example 6

Starting from the compound 16 obtained in the above Synthetic Example 3, the compound 17 of the invention was prepared.

Compound 17

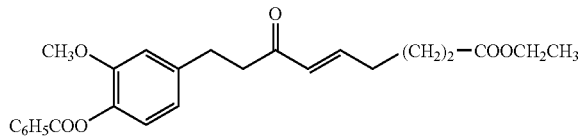

To a solution of 2.33 g (4.01 mmol) of the compound 16 dissolved in 60 g of 1,2-dichloroethane, 20 g of isopropyl alcohol, and 20 g of glycerin were added 0.56 ml (4.02 mmol) of triethylamine, 105 mg (0.400 mmol) of triphenylphosphine, and 232 mg (0.201 mmol) of tetrakistriphenylphosphine palladium, followed by stirring at a bath temperature of 100° C. for 14 hours. After cooling and concentration, 30 ml of distilled water, 20 ml of saturated sodium chloride aqueous solution, and 50 ml of ethyl acetate were added thereto, followed by partitioning. The organic layer was separated and washed with 10 ml of saturated sodium chloride aqueous solution. The combined aqueous layer was extracted with 20 ml of ethyl acetate. The combined organic layer was dried over anhydrous magnesium sulfate. The solvent was removed by distillation and purification by silica gel column chromatography was carried out to obtain 744 mg (yield 44%) of a pale yellow, liquid compound having a medium viscosity.

The chemical shift values of the product on $^1$H-NMR spectrum as measured in deuterochloroform were as follows: 1.25 (3H, t), 1.74-1.86 (2H, m), 2.21-2.40 (4H, m), 2.86-2.99 (4H, m), 3.80 (3H, s), 4.12 (2H, q), 6.13 (1H, d), 6.76-6.88 (3H, m), 7.03-7.08 (1H, d), 7.45-7.54 (2H, m), 7.58-7.65 (1H, m), 8.21 (2H, d).

The wave numbers (cm$^{-1}$) with absorption on IR absorption spectrum (KBr pellet method) were as follows: 2940, 1740, 1670, 1650, 1510, 1270, 1200, 1150, 1060, 1030, 710.

The results of elemental analysis were as follows: carbon 71.00% and hydrogen 6.43%.

Based on the above analysis, it was confirmed that the obtained compound was the compound 17.

Example 7

Starting from the compound 17 obtained in Example 6, a mixture of the compound 18 and the compound 19 of the invention was prepared.

Compound 18

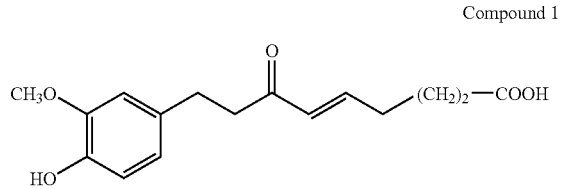

Compound 19

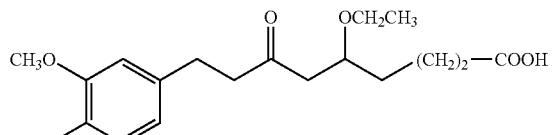

To a solution of 506 mg (0.922 mmol) of the compound 17 dissolved in 5 ml of ethanol was added 5 ml of 1N sodium hydroxide aqueous solution. After 1 hour of stirring, 5 ml of 1N hydrochloric acid was added to terminate the reaction. To the reaction solution was added 50 ml of saturated sodium chloride aqueous solution and extraction with 10 ml of chloroform was repeated three times. The combined organic layer was dried over anhydrous magnesium sulfate and then concentrated. The obtained residue was purified by silica gel column chromatography to obtain 303 mg of a pale yellow, liquid compound having a medium viscosity.

As a result of analyzing $^1$H-NMR spectrum as measured in deuterochloroform, it was confirmed that the product was a mixture of the compound 18 and the compound 19 wherein ethanol used as the solvent was added to the double bond of the compound 18 (existing molar ratio of the compound 18 to the compound 19 was 45:55). Incidentally, the chemical shift value of the ethoxy group in the compound 19 was 1.13 (3H, t) and 3.37-3.50 (2H, m) and the chemical shift value of CH to which the ethoxy group was bonded was 3.68-3.83 (1H, m).

Synthetic Example 4

As starting materials for obtaining the compound of the formula (4), starting from the compound 3 and the compound 20, the compound 21 was prepared.

Compound 20

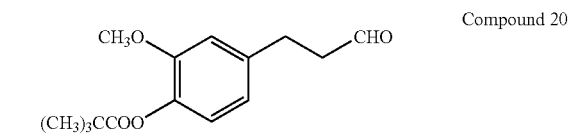

Compound 21

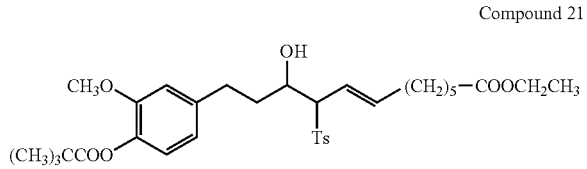

A solution of 11.9 g (35.2 mmol) of the compound 3 dissolved in 100 ml of tetrahydrofuran was cooled to −78° C. with dry ice/acetone. To the resulting solution was dropwise added 26.0 ml (36.4 mmol) of 1.40 M t-butyllithium/n-heptane solution. After the resulting mixture was stirred at the same temperature for 10 minutes, a solution of 9.00 g (34.0 mmol) of the compound 20 dissolved in 50 ml of tetrahydrofuran was dropwise added to the mixture. After dropwise addition, the resulting mixture was stirred at the same temperature for 5 minutes and then, the temperature was gradually elevated. When the temperature of the reaction solution reached −5° C., 30 ml of 10% citric acid aqueous solution was added to terminate the reaction. To the reaction mixture was added 60 ml of saturated sodium chloride aqueous solution, followed by partitioning. The organic layer was separated and the aqueous layer was extracted in 50 ml of ethyl acetate. The combined organic layer was dried over anhydrous magnesium sulfate. The solvent was removed by distillation and purification by silica gel column chromatography was carried out to obtain 6.03 g (yield 29%) of a pale yellow, liquid compound having a medium viscosity.

The chemical shift values of the product on $^1$H-NMR spectrum as measured in deuterochloroform were as follows: 1.17-2.30 (24H, m), 2.45 (3H, s), 2.56-2.92 (2H, m), 3.15-4.58 (8H, m), 4.95-5.83 (2H, m), 6.65-6.94 (3H, m), 7.29-7.38 (2H, m), 7.63-7.77 (2H, m).

The wave numbers (cm$^{-1}$) with absorption on IR absorption spectrum (KBr pellet method) were as follows: 3510, 2970, 2940, 2860, 1750, 1730, 1600, 1510, 1280, 1200, 1120, 1030, 670.

The results of elemental analysis were as follows: carbon 65.51% and hydrogen 7.45%.

Based on the above analysis, it was confirmed that the obtained compound was the compound 21.

Example 8

Starting from the compound 21 obtained in the above Synthetic Example 4, the compound 22 of the invention was prepared.

Compound 22

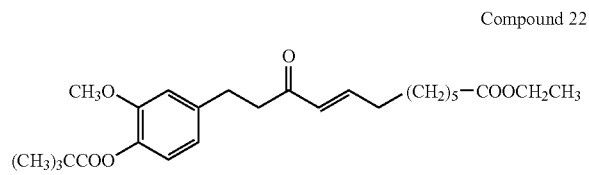

To a solution of 6.00 g (9.95 mmol) of the compound 21 dissolved in 60 g of 1,2-dichloroethane and 15 g of methanol were added 2.10 ml (15.1 mmol) of triethylamine, 130 mg (0.496 mmol) of triphenylphosphine, and 575 mg (0.498 mmol) of tetrakistriphenylphosphine palladium, followed by stirring at a bath temperature of 100° C. for 16 hours. After cooling and concentration, 50 ml of saturated sodium chloride aqueous solution and 50 ml of ethyl acetate were added thereto, followed by partitioning. The organic layer was separated and washed with 10 ml of saturated sodium chloride aqueous solution. The combined aqueous layer was extracted with 30 ml of ethyl acetate. The combined organic layer was dried over anhydrous magnesium sulfate. The solvent was removed by distillation and purification by silica gel column chromatography was carried out to obtain 936 mg (yield 21%) of a pale yellow, liquid compound having a medium viscosity.

The chemical shift values of the product on $^1$H-NMR spectrum as measured in deuterochloroform were as follows: 1.25 (3H, t), 1.29-1.52 (15H, m), 1.57-1.68 (2H, m), 2.16-2.33 (4H, m), 2.82-2.96 (4H, m), 3.80 (3H, s), 4.13 (2H, q), 6.10 (1H, d), 6.70-6.94 (4H, m).

The wave numbers (cm$^{-1}$) with absorption on IR absorption spectrum (KBr pellet method) were as follows: 2970, 2930, 2860, 1750, 1740, 1670, 1630, 1610, 1510, 1270, 1200, 1120, 1040.

The results of elemental analysis were as follows: carbon 70.17% and hydrogen 8.80%.

Based on the above analysis, it was confirmed that the obtained compound was the compound 22.

Example 9

Starting from the compound 22 obtained in Example 8, the compound 23 of the invention was prepared.

Compound 23

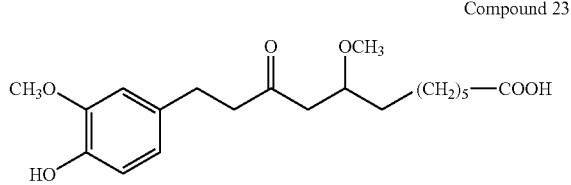

To a solution of 197 mg (0.441 mmol) of the compound 22 dissolved in 3.0 ml of methanol was added 1.5 ml of 1N sodium hydroxide aqueous solution, followed by stirring. After 1 hour of stirring, 1.5 ml of 1N hydrochloric acid was added to the reaction mixture to neutralize it. Then, 30 ml of saturated sodium chloride aqueous solution was added and extraction with 10 ml of chloroform was repeated three times. The combined organic layer was dried over anhydrous magnesium sulfate and then the solvent was removed by distillation. The obtained residue was purified by silica gel column chromatography to obtain 59.7 mg (44%) of a pale yellow, liquid compound having a low viscosity.

The chemical shift values of the product on $^1$H-NMR spectrum as measured in deuterochloroform were as follows: 1.22-1.53 (8H, m), 1.57-1.70 (2H, m), 2.32-2.44 (3H, m), 2.58-2.88 (5H, m), 3.28 (3H, s), 3.60-3.69 (1H, m), 3.87 (3H, s), 5.56 (1H, br), 6.63-6.72 (2H, m), 6.78-6.85 (1H, m).

The wave numbers (cm$^{-1}$) with absorption on IR absorption spectrum (KBr pellet method) were as follows: 3410, 2930, 2860, 1710, 1610, 1520, 1270, 1240, 1150, 1120, 1030, 820, 800.

The results of elemental analysis were as follows: carbon 78.56% and hydrogen 10.05%.

Based on the above analysis, it was confirmed that the obtained compound was the compound 23.

Synthetic Example 5

As starting materials for obtaining the compound of the formula (4), starting from the compound 3 and the compound 24, the compound 25 was prepared.

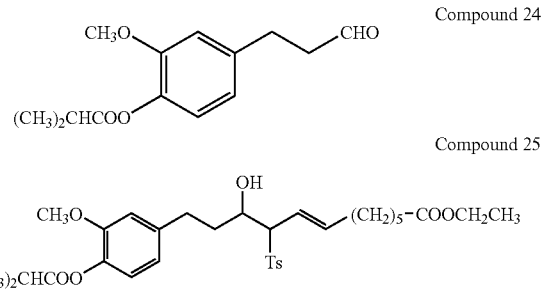

According to the method of Synthetic Example 1, 663 mg (yield 32%) of the compound 25 as a pale yellow, liquid compound having a medium viscosity was obtained from 1.19 g (3.52 mmol) of the compound 3 and 851 mg (3.40 mmol) of the compound 24.

The chemical shift values of the product on $^1$H-NMR spectrum as measured in deuterochloroform were as follows: 1.22-1.60 (18H, m), 1.99-2.45 (4H, m), 2.78 (3H, s), 2.77-2.84 (2H, m), 2.94 (1H, t), 3.71-3.80 (4H, m), 4.12 (2H, q), 5.37-5.43 (1H, m), 5.47-5.53 (1H, m), 6.74-6.94 (3H, m), 7.30-7.35 (2H, m), 7.72-7.77 (2H, m).

The wave numbers (cm$^{-1}$) with absorption on IR absorption spectrum (KBr pellet method) were as follows: 3510, 2970, 2940, 2860, 1750, 1730, 1600, 1510, 1280, 1200, 1120, 1030, 670.

The results of elemental analysis were as follows: carbon 65.28% and hydrogen 7.53%.

Example 10

Starting from the compound 25 obtained in Synthetic Example 5, the compound 26 of the invention was prepared.

Compound 26

According to the method of Example 1, 936 mg (yield 21%) of the compound 26 as a pale yellow, liquid compound having a medium viscosity was obtained from 6 g (9.95 mmol) of the compound 25.

The chemical shift values of the product on $^1$H-NMR spectrum as measured in deuterochloroform were as follows: 1.23-1.73 (17H, m), 2.18-2.31 (4H, m), 2.79-2.93 (5H, m), 3.79 (3H, s), 4.12 (2H, q), 6.09 (1H, d), 6.75-6.83 (3H, m), 6.91 (1H, d).

The wave numbers (cm$^{-1}$) with absorption on IR absorption spectrum (KBr pellet method) were as follows: 2979, 1760, 1732, 1668, 1603, 1512, 1468, 1369, 1267, 1150, 1127, 1038.

The results of elemental analysis were as follows: carbon 69.42% and hydrogen 8.39%.

Example 11

The compound 26 obtained in Example 10 was reduced to obtain the compound 27 of the invention.

Compound 27

A solution of 588 mg (1.36 mmol) of the compound 26 and 1.52 g (4.08 mmol) of cerium chloride heptahydrate dissolved in 24 ml of methanol was cooled to −78° C. with dry ice/acetone. To the solution was added 77.1 mg (2.04 mmol) of sodium borohydride, followed by stirring at the same temperature for 15 minutes. To the reaction mixture were added 40 ml of saturated sodium chloride aqueous solution and 80 ml of ethyl acetate, followed by partitioning. The organic layer was separated and the aqueous layer was extracted with 40 ml of ethyl acetate. The combined organic layer was dried over anhydrous magnesium sulfate. Then, the solvent was removed by distillation and drying under reduced pressure was carried out to obtain 575 mg (97.3%) of a pale yellow, liquid compound having a medium viscosity.

The chemical shift values of the product on $^1$H-NMR spectrum as measured in deuterochloroform were as follows: 1.23-1.64 (17H, m), 1.82-1.84 (2H, m), 2.04 (2H, dd), 2.29 (2H, t), 2.64-2.70 (2H, m), 2.70-2.84 (1H, m), 3.80 (3H, s), 4.07-4.15 (3H, m), 5.46-5.52 (1H, m), 5.61-5.68 (1H, m), 6.75-6.79 (2H, m), 6.90 (1H, d).

The wave numbers (cm$^{-1}$) with absorption on IR absorption spectrum (KBr pellet method) were as follows: 3504, 2974, 1761, 1736, 1606, 1511, 1467, 1418, 1280, 1182, 1127, 1098, 1036.

The results of elemental analysis were as follows: carbon 69.10% and hydrogen 8.81%.

Based on the above analysis, it was confirmed that the obtained compound was the compound 27.

Example 12

The compound 27 obtained in Example 11 was epoxidized to obtain the compound 28 of the invention.

Compound 28

To a solution of 257 mg (0.591 mmol) of the compound 27 dissolved in 9 ml of dichloromethane was dropwise added 204 mg (1.18 mmol) of m-chloroperbenzoic acid dissolved in 3 ml of dichloromethane under ice cooling. After 4 hours of stirring at the same temperature, 10 ml of 10% sodium thiosulfate aqueous solution was added to the reaction mixture and extraction with 10 ml of chloroform was repeated two times. The combined organic layer was dried over anhydrous magnesium sulfate and then the solvent was removed by distillation. The obtained residue was purified by silica gel thin-layer chromatography to obtain 257 mg (97%) of a pale yellow, liquid compound having a medium viscosity.

The chemical shift values of the product on $^1$H-NMR spectrum as measured in deuterochloroform were as follows: 1.23-1.95 (21H, m), 2.29 (2H, t), 2.72-2.91 (5H, m), 3.51-3.53 (1H, m), 3.80 (3H, s), 4.12 (2H, q), 6.76-6.80 (2H, m), 6.92 (1H, d).

The results of elemental analysis were as follows: carbon 66.64% and hydrogen 8.50%.

Based on the above analysis, it was confirmed that the obtained compound was the compound 28.

Example 13

The compound 22 obtained in Example 8 was catalytically hydrogenated to obtain the compound 29 of the invention.

Compound 29

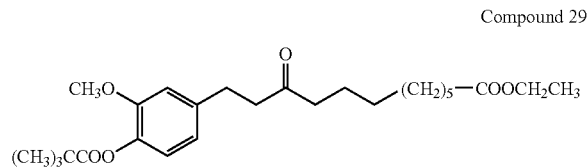

To a solution of 1 g (2.24 mmol) of the compound 22 dissolved in 25 ml of ethanol was added 100 mg of palladium-carbon. After the reaction system was stirred under a hydrogen atmosphere for 3.5 hours, the reaction solution was filtrated through celite to remove the palladium catalyst by filtration. The filtrate was concentrated under reduced pressure to obtain 0.97 g (yield 97%) of a pale yellow, liquid compound having a medium viscosity.

The chemical shift values of the product on $^1$H-NMR spectrum as measured in deuterochloroform were as follows: 1.23-1.61 (24H, m), 2.28 (2H, t), 2.37 (2H, t), 2.71 (1H, t), 2.87 (2H, t), 3.78 (3H, s), 4.12 (2H, q), 6.72-6.77 (2H, m), 6.89 (1H, d).

The wave numbers (cm$^{-1}$) with absorption on IR absorption spectrum (KBr pellet method) were as follows: 2930, 1760, 1730, 1639, 1511, 1452, 1419, 1369, 1267, 1183, 1126.

The results of elemental analysis were as follows: carbon 69.61% and hydrogen 8.99%.

Based on the above analysis, it was confirmed that the obtained compound was the compound 29.

Example 14

The compound 26 obtained in Example 10 was catalytically hydrogenated to obtain the compound 30 of the invention.

Compound 30

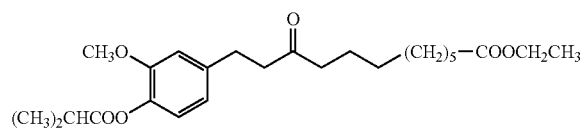

According to the method of Example 13, 148 mg (yield 91%) of the compound 30 as a pale yellow, liquid compound having a medium viscosity was obtained from 161 mg (0.379 mmol) of the compound 26.

The chemical shift values of the compound 30 on $^1$H-NMR spectrum as measured in deuterochloroform were as follows: 1.23-1.71 (21H, m), 2.28 (2H, t), 2.38 (2H, t), 2.43-2.45 (1H, m), 2.72 (2H, t), 2.87 (2H, t), 3.79 (3H, s), 4.12 (2H, q), 6.72-6.78 (2H, m), 6.60 (1H, d).

The wave numbers (cm$^{-1}$) with absorption on IR absorption spectrum (KBr pellet method) were as follows: 2930, 1760, 1730, 1639, 1511, 1452, 1419, 1369, 1267, 1183, 1126, 1098, 1029, 1015.

The results of elemental analysis were as follows: carbon 69.10% and hydrogen 8.81%.

Example 15

The compound 30 obtained in Example 14 was reduced with sodium borohydride to obtain the compound 31 of the invention.

Compound 31

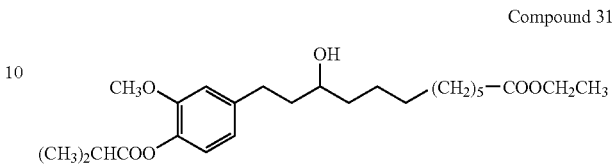

A solution of 188 mg (0.433 mmol) of the compound 30 dissolved in 5 ml of methanol was added 16.4 mg (0.433 mmol) of sodium borohydride under ice cooling. After stirring at room temperature for 2 hours, to the reaction mixture were added 10 ml of saturated sodium chloride aqueous solution and 10 ml of ethyl acetate, followed by partitioning. The organic layer was separated and the aqueous layer was extracted with 10 ml of ethyl acetate. After the combined organic layer was dried over anhydrous magnesium sulfate, the solvent was removed by distillation and drying under reduced pressure was carried out to obtain 187 mg (99%) of a pale yellow, liquid compound having a medium viscosity.

The chemical shift values of the product on $^1$H-NMR spectrum as measured in deuterochloroform were as follows: 1.20-1.72 (28H, m), 2.26 (2H, t), 2.55-2.65 (1H, m), 2.70-2.80 (1H, m), 3.54-3.63 (1H, m), 3.76 (3H, s), 4.09 (2H, q), 6.72-6.75 (2H, m), 6.86 (1H, d).

The wave numbers (cm$^{-1}$) with absorption on IR absorption spectrum (KBr pellet method) were as follows: 3466, 2933, 1739, 1600, 1513, 1465, 1371, 1267, 1142, 1040.

The results of elemental analysis were as follows: carbon 68.78% and hydrogen 9.23%.

Based on the above analysis, it was confirmed that the obtained compound was the compound 31.

Example 16

The compound 26 obtained in Example 10 was ketalized to obtain the compound 32 of the invention.

Compound 32

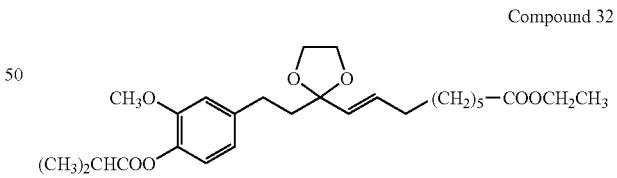

The present reaction was carried out under a nitrogen atmosphere. To a solution of 11 μl (0.0614 mmol) of trimethylsilyl trifluoromethanesulfonate and 0.9 ml (3.69 mmol) of 1,2-bistrimethylsiloxyethane dissolved in 6 ml of dichloromethane was dropwise added a solution of 133 mg (0.307 mmol) of the compound 26 dissolved in 1 ml of dichloromethane under ice cooling. After 50 minutes of stirring, triethylamine was added to the reaction mixture to terminate the reaction. Then, 5 ml of saturated sodium bicarbonate aqueous solution and 5 ml of chloroform were added, followed by partitioning. The organic layer was separated and dried over anhydrous magnesium sulfate and then the solvent was removed by distillation. The obtained residue was purified by silica gel thin-layer chromatography to obtain 114 mg (78%) of a pale yellow, liquid compound having a medium viscosity.

The chemical shift values of the product on $^1$H-NMR spectrum as measured in deuterochloroform were as follows: 1.23-1.64 (17H, m), 1.98-2.06 (4H, m), 2.28 (2H, t), 2.67-2.71 (2H, m), 2.80-2.84 (1H, m), 3.79 (3H, s), 3.91-3.98 (4H, m), 4.12 (2H, q), 5.38 (1H, d), 5.81 (1H, dt), 6.74-6.78 (2H, m), 6.89 (1H, d).

The wave numbers (cm$^{-1}$) with absorption on IR absorption spectrum (KBr pellet method) were as follows: 2924, 1758, 1737, 1608, 1510, 1466, 1420, 1127, 1042.

The results of elemental analysis were as follows: carbon 68.04% and hydrogen 8.46%.

Based on the above analysis, it was confirmed that the obtained compound was the compound 32.

Example 17

The compound 29 obtained in Example 13 was ketalized to obtain the compound 33 of the invention.

Compound 33

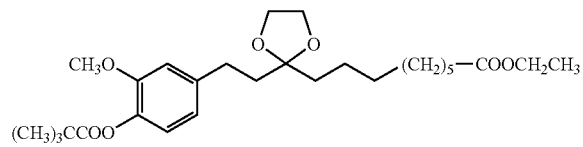

According to the method of Example 16, 200 mg (78%) of the compound 33 as a pale yellow, liquid compound having a medium viscosity was obtained from 234 mg (0.522 mmol) of the compound 29.

The chemical shift values of the product on $^1$H-NMR spectrum as measured in deuterochloroform were as follows: 1.23-1.35 (22H, m), 1.59-1.64 (4H, m), 1.90-1.94 (2H, m), 2.28 (2H, t), 2.64-2.68 (2H, m), 3.78 (3H, s), 3.98 (4H, s), 4.12 (2H, q), 6.74-6.78 (2H, m), 6.88 (1H, d).

The wave numbers (cm$^{-1}$) with absorption on IR absorption spectrum (KBr pellet method) were as follows: 2936, 1755, 1735, 1606, 1511, 1464, 1418, 1266, 1203, 1117, 1036.

The results of elemental analysis were as follows: carbon 68.54% and hydrogen 8.63%.

Example 18

Water molecule was added to the compound 26 obtained in Example 10 and removal of the protective group of the phenolic hydroxyl group and the protective group of the carboxyl group was carried out to obtain the compound 34 of the invention.

Compound 34

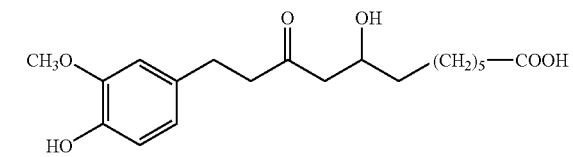

To a solution of 43 mg (99.4 μmol) of the compound 26 dissolved in 3 ml of toluene were added 2 ml of 1N sodium hydroxide aqueous solution and 3.5 mg (9.9 μmol) of benzyltributylammonium bromide, followed by 18 hours of stirring at room temperature. The organic layer was separated and 1N hydrochloric acid was added to the aqueous layer to neutralize it. The aqueous layer was extracted with 5 ml of chloroform three times. The combined organic layer was dried over anhydrous magnesium sulfate and then the solvent was removed by distillation. The obtained residue was purified by silica gel thin-layer chromatography to obtain 23.2 mg (66%) of a yellow, liquid compound having a medium viscosity.

The chemical shift values of the product on $^1$H-NMR spectrum as measured in deuterochloroform were as follows: 1.00-1.77 (10H, m), 2.18-2.33 (2H, m), 2.65 (2H, t), 2.88 (2H, t), 3.20-3.24 (2H, m), 3.72-3.86 (4H, m) 4.75 (1H, s), 5.30 (1H, br), 6.68-6.72 (2H, m), 6.83 (1H, d).

The wave numbers (cm$^{-1}$) with absorption on IR absorption spectrum (KBr pellet method) were as follows: 3336, 2943, 1723, 1710, 1603, 1514, 1426, 1275, 1212.

The results of elemental analysis were as follows: carbon 64.75% and hydrogen 8.01%.

Based on the above analysis, it was confirmed that the obtained compound was the compound 34.

Example 19

The compound 34 obtained in Example 18 was reduced to obtain the compound 35 of the invention.

Compound 35

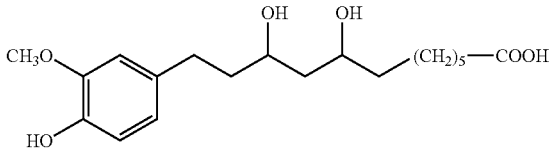

A solution of 35.2 mg (0.103 mmol) of the compound 34 dissolved in 2 ml of methanol was added 5.8 mg (0.154 mmol) of sodium borohydride under ice cooling. After stirring at a bath temperature of 60° C. for 6 hours, 5 ml of saturated sodium chloride aqueous solution and 5 ml of ethyl acetate were added to the reaction mixture, followed by partitioning. The organic layer was separated and the aqueous layer was extracted with 5 ml of ethyl acetate three times. After the combined organic layer was dried over anhydrous magnesium sulfate and the solvent was removed by distillation. The obtained residue was purified by silica gel thin-layer chromatography to obtain 7.4 mg (21%) of a colorless crystalline compound.

The chemical shift values of the product on $^1$H-NMR spectrum as measured in deuteromethanol were as follows: 1.10-1.90 (12H, m), 2.18-2.33 (2H, m), 2.39-2.43 (2H, m), 2.79-2.83 (2H, m), 3.64-3.87 (4H, m), 6.65-6.68 (2H, m), 6.74 (1H, d).

The wave numbers (cm$^{-1}$) with absorption on IR absorption spectrum (KBr pellet method) were as follows: 3448, 2924, 1701, 1621, 1560, 1524, 1410, 1212, 1127, 1098, 1028.

The results of elemental analysis were as follows: carbon 64.38% and hydrogen 8.53%.

Based on the above analysis, it was confirmed that the obtained compound was the compound 35.

Example 20

Methanol was added to the compound 26 obtained in Example 10 and removal of the protective group of the phenolic hydroxyl group was carried out to obtain the compound 36 of the invention.

Compound 36

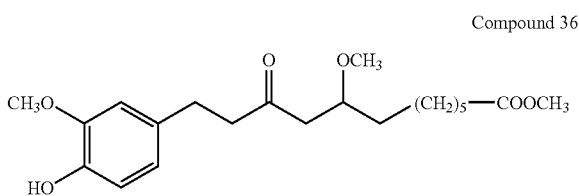

To a solution of 432 mg (0.999 mmol) of the compound 26 dissolved in 6 ml of methanol were added a solution of 80 mg (2 mmol) of sodium hydroxide previously dissolved in 4 ml of methanol. After 4 hours of stirring at room temperature, 1N hydrochloric acid was added to effect neutralization. After the solvent was removed by distillation, 10 ml of saturated sodium chloride aqueous solution was added to the obtained residue and the mixture was extracted with 10 ml of ethyl acetate three times. The combined organic layer was dried over anhydrous magnesium sulfate and then the solvent was removed by distillation. The obtained residue was purified by silica gel thin-layer chromatography to obtain 154 mg (41%) of a pale yellow, liquid compound having a medium viscosity.

The chemical shift values of the product on $^1$H-NMR spectrum as measured in deuterochloroform were as follows: 1.29-1.63 (10H, m), 2.30 (2H, t), 2.39 (2H, dd), 2.64 (1H, dd), 2.73-2.76 (2H, m), 2.81-2.83 (2H, m), 3.25 (3H, s), 3.64-3.67 (4H, m), 3.88 (3H, s), 5.51 (1H, s), 6.66-6.70 (2H, m), 6.82 (1H, d).

The wave numbers (cm$^{-1}$) with absorption on IR absorption spectrum (KBr pellet method) were as follows: 3413, 2931, 1733, 1604, 1515, 1436, 1364, 1267, 1238, 1196, 1155, 1127, 1084, 1072, 1028.

The results of elemental analysis were as follows: carbon 66.29% and hydrogen 8.48%.

Based on the above analysis, it was confirmed that the obtained compound was the compound 36.

Example 21

The compound 27 obtained in Example 11 was hydrolyzed to obtain the compound 37 of the invention.

Compound 37

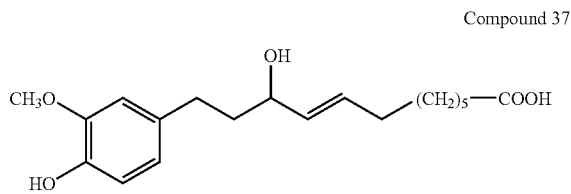

To a solution of 209 mg (0.480 mmol) of the compound 27 dissolved in 4 ml of ethanol was added 2 ml of 1N sodium hydroxide aqueous solution, followed by stirring. After 6 hours of stirring at a bath temperature of 80° C., 1N hydrochloric acid was added to effect neutralization. After the reaction solution was concentrated under reduced pressure and ethanol was removed by distillation, 10 ml of saturated sodium chloride aqueous solution was added and the mixture was extracted with 10 ml of ethyl acetate three times. The combined organic layer was dried over anhydrous magnesium sulfate and then the solvent was removed by distillation. The obtained residue was purified by silica gel thin-layer chromatography to obtain 100 mg (62%) of a pale yellow, liquid compound having a medium viscosity.

The chemical shift values of the product on $^1$H-NMR spectrum as measured in deuterochloroform were as follows: 1.12-2.35 (14H, m), 2.60-2.90 (2H, m), 3.86 (3H, s), 4.07-4.13 (1H, m), 5.36-5.53 (1H, m), 5.59-5.67 (1H, m), 6.64-6.70 (2H, m), 6.81 (1H, d).

The wave numbers (cm$^{-1}$) with absorption on IR absorption spectrum (KBr pellet method) were as follows: 3403, 2926, 2858, 2368, 1700, 1515, 1417, 1274, 1034.

The results of elemental analysis were as follows: carbon 67.83% and hydrogen 8.39%.

Based on the above analysis, it was confirmed that the obtained compound was the compound 37.

Example 22

The compound 30 obtained in Example 14 was hydrolyzed to obtain the compound 38 of the invention.

Compound 38

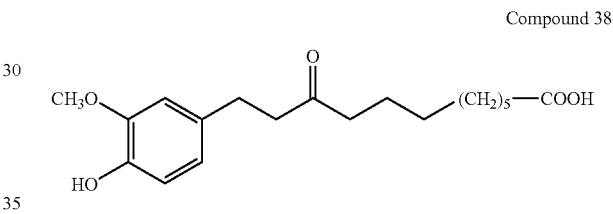

According to the method of Example 21, 136 mg (89%) of the compound 38 as a colorless crystalline compound was obtained from 199 mg (0.457 mmol) of the compound 30.

The chemical shift values of the compound 38 on $^1$H-NMR spectrum as measured in deuterochloroform were as follows: 1.11-1.64 (12H, m), 2.32-2.38 (4H, m), 2.69 (2H, t), 2.82 (2H, t), 3.87 (3H, s), 5.55 (1H, br), 6.65-6.69 (2H, m), 6.81 (1H, d).

The wave numbers (cm$^{-1}$) with absorption on IR absorption spectrum (KBr pellet method) were as follows: 3414, 2935, 1703, 1611, 1520, 1466, 1409, 1279, 1228, 1122, 1028.

The results of elemental analysis were as follows: carbon 67.83% and hydrogen 8.39%.

Example 23

The compound 31 obtained in Example 15 was hydrolyzed to obtain the compound 39 of the invention.

Compound 39

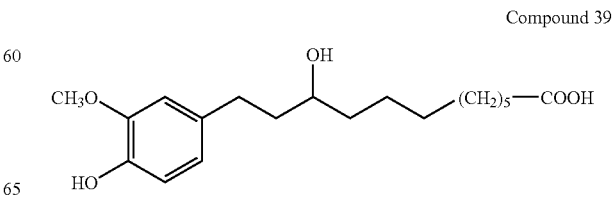

According to the method of Example 21, 134 mg (91%) of the compound 39 as a colorless crystalline compound was obtained from 187 mg (0.433 mmol) of the compound 31.

The chemical shift values of the compound 39 on $^1$H-NMR spectrum as measured in deuterochloroform were as follows: 1.23-1.77 (16H, m), 2.33 (2H, t), 2.56-2.63 (1H, m), 2.68-2.74 (1H, m), 3.59-3.66 (1H, m), 3.87 (3H, s), 5.50 (1H, br), 6.67-6.70 (2H, m), 6.82 (1H, d).

The wave numbers (cm$^{-1}$) with absorption on IR absorption spectrum (KBr pellet method) were as follows: 3413, 2931, 1705, 1612, 1515, 1435, 1367, 1264, 1154, 1038.

The results of elemental analysis were as follows: carbon 67.43% and hydrogen 8.93%.

Example 24

The compound 22 obtained in Example 8 was reduced with lithium aluminum hydride to obtain the compound 40 of the invention.

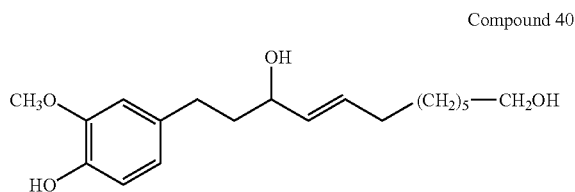

Compound 40

To a solution of 594 mg (1.33 mmol) of the compound 22 dissolved in 40 ml of tetrahydrofuran was added 202 mg (5.32 mmol) of lithium aluminum hydride. After 1 hour of stirring at room temperature, 1N hydrochloric acid was added to the reaction mixture to terminate the reaction. Then, 15 ml of distilled water was added and extraction with 20 ml of ethyl acetate was repeated twice. The combined organic layer was dried over anhydrous magnesium sulfate and then the solvent was removed by distillation. The obtained residue was purified by silica gel column chromatography to obtain 315 mg (73%) of a colorless, liquid compound having a medium viscosity.

The chemical shift values of the product on $^1$H-NMR spectrum as measured in deuterochloroform were as follows: 1.23-1.83 (12H, m), 2.02 (2H, m), 2.56-2.69 (2H, m), 3.61 (2H, t), 3.84 (3H, s), 4.04 (1H, dd), 5.45-5.49 (1H, m), 5.58-5.66 (1H, m), 6.65-6.67 (2H, m), 6.79 (1H, d).

The wave numbers (cm$^{-1}$) with absorption on IR absorption spectrum (KBr pellet method) were as follows: 3349, 2930, 1666, 1602, 1516, 1464, 1453, 1431, 1368, 1273, 1236, 1154, 1036.

The results of elemental analysis were as follows: carbon 70.77% and hydrogen 9.38%.

Based on the above analysis, it was confirmed that the obtained compound was the compound 40.

Example 25

The compound 40 obtained in Example 24 was epoxidized to obtain the compound 41 of the invention.

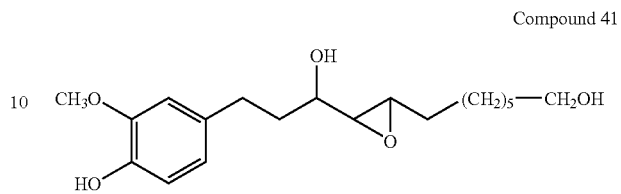

Compound 41

To a solution of 87.3 mg (0.271 mmol) of the compound 40 dissolved in 5 ml of dichloromethane was dropwise added 93.6 mg (0.542 mmol) of m-chloroperbenzoic acid dissolved in 3 ml of dichloromethane under ice cooling. After 6.5 hours of stirring at the same time, 5 ml of 10% sodium thiosulfate aqueous solution was added to the reaction mixture and extraction with 5 ml of chloroform was repeated two times. The combined organic layer was dried over anhydrous magnesium sulfate and then the solvent was removed by distillation. The obtained residue was purified by silica gel thin-layer chromatography to obtain 44.6 mg (49%) of a pale yellow, liquid compound having a medium viscosity.

The chemical shift values of the product on $^1$H-NMR spectrum as measured in deuterochloroform were as follows: 1.33-2.30 (15H, m), 2.64-3.10 (4H, m), 3.62 (2H, t), 3.80-3.87 (4H, m), 6.68-6.71 (2H, m), 6.82 (1H, d).

The wave numbers (cm$^{-1}$) with absorption on IR absorption spectrum (KBr pellet method) were as follows: 3394, 2931, 1723, 1603, 1517, 1453, 1430, 1368, 1270, 1035.

The results of elemental analysis were as follows: carbon 67.83% and hydrogen 8.39%.

Based on the above analysis, it was confirmed that the obtained compound was the compound 41.

Example 26

The compound 30 obtained in Example 14 was reduced with lithium aluminum hydride to obtain the compound 42 of the invention.

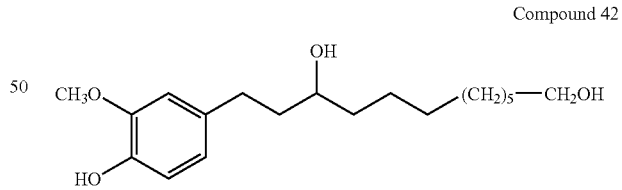

Compound 42

According to the method of Example 24, 97.4 mg (91%) of the compound 42 as a colorless crystalline compound was obtained from 148 mg (0.330 mmol) of the compound 30.

The chemical shift values of the product on $^1$H-NMR spectrum as measured in deuterochloroform were as follows: 1.26-1.72 (18H, m), 2.54-2.61 (1H, m), 2.66-2.70 (1H, m), 3.54-3.73 (3H, m), 3.85 (3H, s), 6.66-6.68 (2H, m), 6.80 (1H, d).

The wave numbers (cm$^{-1}$) with absorption on IR absorption spectrum (KBr pellet method) were as follows: 3426, 2930, 1607, 1515, 1481, 1468, 1437, 1365, 1268, 1239, 1155, 1124, 1039.

The results of elemental analysis were as follows: carbon 70.33% and hydrogen 9.94%.

Example 27

The compound 32 obtained in Example 16 was reduced with lithium aluminum hydride to obtain the compound 43 of the invention.

Compound 43

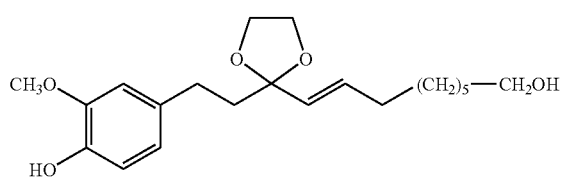

To a solution of 159 mg (0.334 mmol) of the compound 32 dissolved in 6 ml of tetrahydrofuran was added 50.0 mg (1.33 mmol) of lithium aluminum hydride under ice cooling. After 1 hour of stirring at room temperature, 1N hydrochloric acid was added to the reaction mixture to terminate the reaction. Then, 5 ml of saturated sodium chloride aqueous solution was added and extraction with 5 ml of ethyl acetate was repeated three times. The combined organic layer was dried over anhydrous magnesium sulfate and then the solvent was removed by distillation. The obtained residue was purified by silica gel thin-layer chromatography to obtain 121 mg (99%) of a yellow, liquid compound having a medium viscosity.

The chemical shift values of the product on $^1$H-NMR spectrum as measured in deuterochloroform were as follows: 1.26-1.55 (10H, m), 1.96-2.06 (4H, m), 2.62-2.66 (2H, m), 3.62 (2H, t), 3.86 (3H, s), 3.91-3.99 (4H, m), 5.38 (1H, d), 5.61 (1H, s), 5.81 (1H, dt), 6.66-6.69 (2H, m), 6.82 (1H, d).

The results of elemental analysis were as follows: carbon 69.20% and hydrogen 8.85%.

Based on the above analysis, it was confirmed that the obtained compound was the compound 43.

Example 28

The compound 33 obtained in Example 17 was reduced with lithium aluminum hydride to obtain the compound 44 of the invention.

Compound 44

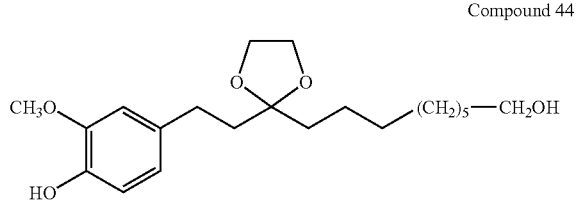

According to the method of Example 27, 137 mg (99%) of the compound 44 as a yellow, liquid compound having a medium viscosity was obtained from 186 mg (0.378 mmol) of the compound 33.

The chemical shift values of the compound 44 on $^1$H-NMR spectrum as measured in deuterochloroform were as follows: 1.24-1.70 (16H, m), 1.88-1.93 (2H, m), 2.59-2.63 (2H, m), 3.64 (2H, t), 3.87 (3H, s), 3.98 (4H, s), 5.50 (1H, br), 6.67-6.70 (2H, m), 6.82 (1H, d).

The results of elemental analysis were as follows: carbon 69.20% and hydrogen 8.85%.

Example 29

The ketal of the compound 43 obtained in Example 27 was removed to obtain the compound 45 of the invention.

Compound 45

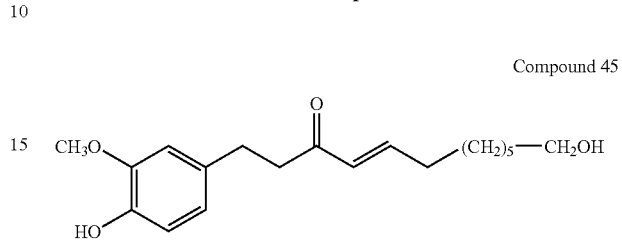

To a solution of 122 mg (0.335 mmol) of the compound 43 dissolved in 2 ml of acetone and 2 ml of distilled water was added 8.4 mg (0.0335 mmol) of pyridinium p-toluenesulfonate. The reaction solution was heated under reflux over a period of 3 hours. After the reaction solution was allowed to cool to room temperature, the solvent was removed by distillation. To the obtained residue was added 5 ml of saturated sodium chloride aqueous solution, and extraction with 5 ml of ethyl acetate was repeated three times. The combined organic layer was dried over anhydrous magnesium sulfate and then the solvent was removed by distillation. The obtained residue was purified by silica gel thin-layer chromatography to obtain 85.2 mg (80%) of a pale yellow, liquid compound having a medium viscosity.

The chemical shift values of the product on $^1$H-NMR spectrum as measured in deuterochloroform were as follows: 1.30-1.58 (10H, m), 2.17 (2H, dd), 2.81-2.86 (4H, m), 3.63 (2H, t), 3.86 (3H, s), 5.73 (1H, s), 6.08 (1H, dt), 6.67-6.71 (2H, m), 6.78-6.83 (2H, m).

The results of elemental analysis were as follows: carbon 71.22% and hydrogen 8.81%.

Based on the above analysis, it was confirmed that the obtained compound was the compound 45.

Example 30

The ketal of the compound 44 obtained in Example 28 was removed to obtain the compound 46 of the invention.

Compound 46

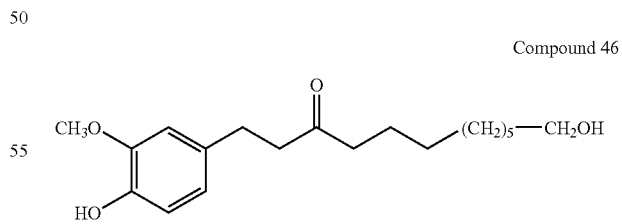

According to the method of Example 29, 120 mg (99%) of the compound 46 as a colorless crystalline compound was obtained from 137 mg (0.377 mmol) of the compound 44.

The chemical shift values of the compound 46 on $^1$H-NMR spectrum as measured in deuterochloroform were as follows: 1.20-1.51 (14H, m), 2.29 (2H, t), 2.62 (2H, t), 2.75 (2H, t), 3.59 (2H, t), 3.81 (3H, s), 5.47 (1H, s), 6.64-6.67 (2H, m), 6.80 (1H, d).

The wave numbers (cm$^{-1}$) with absorption on IR absorption spectrum (KBr pellet method) were as follows: 3415, 2920, 1705, 1611, 1520, 1463, 1455, 1365, 1278, 1236, 1151, 1122, 1064, 1028.

The results of elemental analysis were as follows: carbon 70.77% and hydrogen 9.38%.

Example 31

The compound 28 obtained in Example 12 was reduced to obtain the compound 47 of the invention.

Compound 47

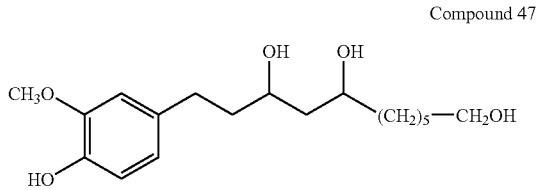

To a solution of 117 mg (0.260 mmol) of the compound 28 dissolved in 10 ml of tetrahydrofuran was added 59.1 mg (1.56 mmol) of lithium aluminum hydride under ice cooling. After 1 hour of stirring at room temperature, 1N hydrochloric acid was added to the reaction mixture to terminate the reaction. Then, 5 ml of saturated sodium chloride aqueous solution was added and extraction with 10 ml of ethyl acetate was repeated three times. The combined organic layer was dried over anhydrous magnesium sulfate and then the solvent was removed by distillation. The obtained residue was purified by silica gel thin-layer chromatography to obtain 81.4 mg (92%) of a colorless crystalline compound.

The chemical shift values of the product on $^1$H-NMR spectrum as measured in deuterochloroform were as follows: 1.24-1.78 (16H, m), 3.63-3.70 (3H, m), 3.88-3.96 (4H, m), 5.49 (1H, s), 6.69-6.73 (2H, m), 6.84 (1H, d).

The wave numbers (cm$^{-1}$) with absorption on IR absorption spectrum (KBr pellet method) were as follows: 3416, 2930, 1653, 1609, 1516, 1453, 1429, 1368, 1274, 1239, 1154, 1030.

The results of elemental analysis were as follows: carbon 67.03% and hydrogen 9.47%.

Based on the above analysis, it was confirmed that the obtained compound was the compound 47.

Example 32

The compound 36 obtained in Example 20 was reduced with lithium aluminum hydride to obtain the compound 48 of the invention.

Compound 48

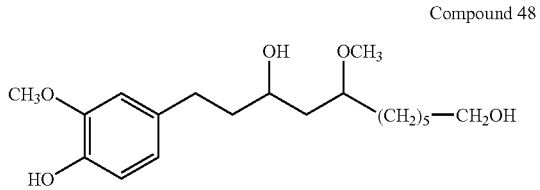

According to the method of Example 24, 97.1 mg (68%) of the compound 48 as a colorless, liquid compound having a medium viscosity was obtained from 154 mg (0.405 mmol) of the compound 36.

The chemical shift values of the compound 48 on $^1$H-NMR spectrum as measured in deuterochloroform were as follows: 1.26-1.80 (14H, m), 2.58-2.64 (1H, m), 2.68-2.74 (1H, m), 3.35-3.63 (4H, m), 3.61 (2H, t), 3.79-3.89 (4H, m), 5.78 (1H, s), 6.67-6.73 (2H, m), 6.81 (1H, d).

The wave numbers (cm$^{-1}$) with absorption on IR absorption spectrum (KBr pellet method) were as follows: 3389, 2932, 2857, 1602, 1516, 1453, 1428, 1371, 1272, 1238, 1084, 1036.

The results of elemental analysis were as follows: carbon 68.15% and hydrogen 9.15%.

Test Example 1

Using the compound 7 obtained in Example 2, the compound 13 obtained in Example 5, a mixture of the compound 18 and the compound 19 (existing molar ratio 45:55) obtained in Example 7, and arbutin (manufactured by Tokyo Kasei Kogyo Co., Ltd.) as a comparative control, a tyrosinase activity inhibition test was carried out using L-dopa as a substrate.

The specific test procedures are as follows.

(1) 1.80 ml of a phosphate buffer prepared by dissolving 1.000 g of sodium dihydrogen phosphate and 1.186 g of disodium hydrogen phosphate in 500 ml of distilled water, 1.00 ml of a substrate solution prepared by dissolving 32.7 mg of L-DOPA in 200 ml of distilled water, and 0.10 ml of a test solution prepared by dissolving the test compound in dimethyl sulfoxide were mixed together.

(2) 0.10 ml of an enzyme solution prepared by dissolving 3.0 mg (2400 units; manufactured by Sigma Corporation) of mushroom tyrosinase in 7.0 ml of distilled water was added to the solution prepared in (1), and the whole was stirred for 15 seconds. The resulting solution was maintained at 25° C., and the absorbance at 475 nm was measured one minute and 45 seconds later and 2 minutes and 45 seconds later.

(3) The test operations in the above (1) and (2) were conducted three times for the individual test compounds and blank test (only dimethyl sulfoxide), and the resulting numeric value was inserted in the following calculation formula and a mean value thereof was regarded as a tyrosinase activity inhibition ratio (%).

Tyrosinase activity inhibition ratio (%)=[($T^1$-$T^2$)/$T^1$]×100

$T^1$=difference in absorbance of solution with addition of no test compound between 2 minutes and 45 seconds later and one minute and 45 seconds later $T^2$=difference in absorbance of solution with addition of test compound was added between 2 minutes and 45 seconds later and one minute and 45 seconds later Table 1 shows the results in the case that the compounds of the invention and arbutin were individually used in the enzymatic reaction solution in amounts of 0.5 mg/ml and 1 mg/ml.

TABLE 1

| | Tyrosinase activity inhibition ratio (%) | |
|---|---|---|
| | 0.5 mg/mL | 1 mg/mL |
| Compound 7 | 59.8 | 77.1 |
| Compound 13 | 58.5 | 76.5 |

TABLE 1-continued

| | Tyrosinase activity inhibition ratio (%) | |
|---|---|---|
| | 0.5 mg/mL | 1 mg/mL |
| Mixture of Compounds 18 and 19 | 47.5 | 71.7 |
| Arbutin | 36.2 | 42.2 |

As a result of the test, it was found that the compounds of the invention each had an effect superior to that of arbutin as a known tyrosinase activity inhibitor.

Test Example 2

Using the compound 40 obtained in Example 24 and arbutin (manufactured by Tokyo Kasei Kogyo Co., Ltd.) as a comparative control, a tyrosinase activity inhibition test was carried out using L-dopa as a substrate. The test procedure was in accordance with Test Example 1.

Table 2 shows the results in the case that the compounds of the invention and arbutin were individually used in the enzymatic reaction solution in amounts of 0.125 mg/ml, 0.250 mg/ml, and 0.50 mg/ml.

TABLE 2

| | Tyrosinase activity inhibition ratio (%) | | |
|---|---|---|---|
| Test compound | 0.5 mg/mL | 0.25 mg/mL | 0.125 mg/mL |
| Compound 40 | 45.3 | 36.5 | 25.5 |
| Arbutin | 34.6 | 28.5 | 23.1 |

As a result of the test, it was found that the compound 40 of the invention had an effect superior to that of arbutin as a known tyrosinase activity inhibitor.

Test Example 3

Using the compound 37 obtained in Example 21, the compound 38 obtained in Example 22, the compound 39 obtained in Example 23, and arbutin (manufactured by Tokyo Kasei Kogyo Co., Ltd.) as a comparative control, a tyrosinase activity inhibition test was carried out using L-dopa as a substrate.

The specific test procedures are as follows.
(1) 72 µl of a phosphate buffer prepared by dissolving 1.000 g of sodium dihydrogen phosphate and 1.186 g of disodium hydrogen phosphate in 500 ml of distilled water, 80 µl of a substrate solution prepared by dissolving 32.7 mg of L-DOPA in 200 ml of distilled water, and 8 µl of a test solution prepared by dissolving the test compound in dimethyl sulfoxide were mixed together.
(2) 80 µl of an enzyme solution prepared by dissolving 3.0 mg (2400 units; manufactured by Sigma Corporation) of mushroom tyrosinase in 7.0 ml of distilled water and diluting the solution with the above phosphate buffer so as to make it five times in amount was added to the solution prepared in (1), and the whole was stirred for 15 seconds. The resulting solution was maintained at 25° C., and the absorbance at 490 nm was measured by a microplate reader one minute and 45 seconds later and 2 minutes and 45 seconds later.
(3) The test operations in the above (1) and (2) were conducted four times for the individual test compounds and blank test (only dimethyl sulfoxide), and the resulting numeric value was inserted in the following calculation formula and a mean value thereof was regarded as a tyrosinase activity inhibition ratio (%).

$$\text{Tyrosinase activity inhibition ratio (\%)} = [(T^1 - T^2)/T^1] \times 100$$

$T^1$ = difference in absorbance of solution with addition of no test compound between 2 minutes and 45 seconds later and one minute and 45 seconds later $T^2$ = difference in absorbance of solution with addition of test compound was added between 2 minutes and 45 seconds later and one minute and 45 seconds later Table 3 shows the results in the case that the compounds of the invention and arbutin were individually used in the enzymatic reaction solution in amounts of 0.5 mg/ml and 1.00 mg/ml.

TABLE 3

| | Tyrosinase activity inhibition ratio (%) | |
|---|---|---|
| Test compound | 1 mg/mL | 0.5 mg/mL |
| Compound 37 | 67.7 | 48.6 |
| Compound 38 | 73.3 | 49.9 |
| Compound 39 | 75.2 | 51.3 |
| Arbutin | 41.6 | 35.0 |

As a result of the test, it was found that the compounds 37, 38, and 39 of the invention each had an effect superior to that of arbutin as a known tyrosinase activity inhibitor.

Test Example 4

Using the compound 42 obtained in Example 26, the compound 45 obtained in Example 29, the compound 46 obtained in Example 30, and arbutin (manufactured by Tokyo Kasei Kogyo Co., Ltd.) as a comparative control, a tyrosinase activity inhibition test was carried out using L-dopa as a substrate. The test procedure was in accordance with Test Example 3.

Table 4 shows the results in the case that the compounds of the invention and arbutin were individually used in the enzymatic reaction solution in amounts of 0.031 mg/ml, 0.063 mg/ml, and 0.125 mg/ml.

TABLE 4

| | Tyrosinase activity inhibition ratio (%) | | |
|---|---|---|---|
| Test compound | 0.125 mg/mL | 0.063 mg/mL | 0.031 mg/mL |
| Compound 42 | 40.6 | 31.3 | 20.1 |
| Compound 45 | 27.6 | 18.2 | 10.7 |
| Compound 46 | 36.9 | 23.8 | 14.9 |
| Arbutin | 24.7 | 17.7 | 10.7 |

As a result of the test, it was found that the compounds 42, 45, and 46 of the invention had effects superior to that of arbutin as a known tyrosinase activity inhibitor.

Test Example 5

Using the compound 34 obtained in Example 18, the compound 47 obtained in Example 31, and arbutin (manufactured by Tokyo Kasei Kogyo Co., Ltd.) as a comparative control, a tyrosinase activity inhibition test was carried out using L-dopa as a substrate. The test procedure was in accordance with Test Example 3.

Table 5 shows the results in the case that the compounds of the invention and arbutin were individually used in the enzymatic reaction solution in an amount of 1.00 mg/ml.

TABLE 5

| Test compound | Tyrosinase activity inhibition ratio (%) |
|---|---|
| Compound 34 | 60.1 |
| Compound 47 | 57.5 |
| Arbutin | 45.6 |

As a result of the test, it was found that the compounds 34 and 47 of the invention each had an effect superior to that of arbutin as a known tyrosinase activity inhibitor.

Test Example 6

Using the compound 48 obtained in Example 32 and arbutin (manufactured by Tokyo Kasei Kogyo Co., Ltd.) as a comparative control, a tyrosinase activity inhibition test was carried out using L-dopa as a substrate. The test procedure was in accordance with Test Example 3.

Table 6 shows the results in the case that the compound of the invention and arbutin were individually used in the enzymatic reaction solution in amounts of 0.25 mg/ml and 0.50 mg/ml.

TABLE 6

| Test compound | Tyrosinase activity inhibition ratio (%) | |
|---|---|---|
| | 0.5 mg/mL | 0.25 mg/mL |
| Compound 48 | 47.1 | 38.2 |
| Arbutin | 42.6 | 35.8 |

As a result of the test, it was found that the compound 48 of the invention had an effect superior to that of arbutin as a known tyrosinase activity inhibitor.

Test Example 7

Using the compound 7 obtained in Example 2, the compound 34, and magnesium ascorbate phosphate as a comparative control, a hyaluronic acid-degrading enzyme activity inhibition test was carried out.

Specific Test Procedure was as Follows.

First, the following solutions shown in A to H were each prepared.

A: 0.1M acetate buffer solution was prepared by dissolving 0.60 g of acetic acid in 100 ml of distilled water.
B: A hyaluronidase solution was prepared by dissolving 7.2 mg of a hyaluronic acid-degrading enzyme (derived from bovine testicles manufactured by Sigma Corporation, Type IV-S) into 3.0 ml of the acetate buffer (prepared in the above A).
C: An activator solution was prepared by dissolving 1.0 mg of compound 48/80 (a hyaluronidase activator manufactured by Sigma Corporation) into 10.0 ml of the acetate buffer (prepared in the above A).
D: A hyaluronic acid solution was prepared by dissolving 12.0 mg of potassium hyaluronate (manufactured by Wako Pure Chemical Industries, Ltd.) into 15.0 ml of the acetate buffer (prepared in the above A).
E: A 0.4N sodium hydroxide aqueous solution was prepared by dissolving 1.60 g of sodium hydroxide into 100 ml of distilled water.
F: After 4.95 g of boric acid was dissolved into 50 ml of distilled water, a 1N sodium hydroxide aqueous solution was added until pH reached 9.1. Subsequently, the whole amount was made 100 ml by adding distilled water.
G: 1.0 g of p-dimethylaminobenzaldehyde, 1.25 ml of 10N hydrochloric acid, and 8.75 ml of acetic acid were mixed. The solution was used after the whole amount was made 100 ml by adding acetic acid immediately before use.
H: Each test compound was dissolved in the acetate buffer (prepared in the above A) so the final test concentration became 0.5 mg/ml and 1.0 mg/ml.

Next, the experimental operation was carried out with the procedures shown in the following (1) to (8).

(1) 0.2 ml of the test compound solution (prepared in the above H) and 0.1 ml of the hyaluronic acid-degrading enzyme solution (prepared in the B) were mixed and the whole was incubated at 37° C. for 20 minutes.
(2) To the above reaction solution was added 0.2 ml of the activator solution (prepared in the above C) and the whole was incubated at 37° C. for 20 minutes.
(3) To the above reaction solution was added 0.5 ml of the hyaluronic acid solution (prepared in the above D), and the whole was incubated at 37° C. for 40 minutes.
(4) To the above reaction solution was added 0.2 ml of the 0.4N sodium hydroxide aqueous solution (prepared in the above E), and the whole was cooled in an ice bath.
(5) To the above reaction solution was added 0.2 ml of the boric acid solution (prepared in the above F), and the whole was heated at 100° C. for 3 minutes.
(6) The above reaction solution was cooled in an ice bath.
(7) To the above reaction solution was added 3.0 ml of the p-dimethylaminobenzaldehyde solution (prepared in the above G), and the whole was incubated at 37° C. for 20 minutes.
(8) Absorbance of the reaction solution at 585 nm was measured using a spectrophotometer.

The above experimental operations were repeated three times, and the resulting numeric value was inserted in the following calculation formula and a mean value thereof was regarded as a hyaluronic acid-degrading enzyme activity inhibition ratio (%).

Hyaluronic acid-degrading enzyme activity inhibition ratio $(\%)=(A-B)/A \times 100$ A=absorbance obtained at the time when operation was carried out with addition of no test compound
B=absorbance obtained at the time when operation was carried out with addition of test compound The compounds of the invention and magnesium ascorbate phosphate were each used in an enzymatic reaction solution in amounts of 0.1 mg/ml, 0.2 mg/ml, and 0.4 mg/ml, and the results were shown in Table 7 (since the compound 7 was not dissolved in a concentration of 0.4 mg/ml, the test was not carried out).

TABLE 7

| | Hyaluronic acid-degrading enzyme activity inhibition ratio (%) | | |
|---|---|---|---|
| | 0.1 mg/mL | 0.2 mg/mL | 0.4 mg/mL |
| Compound 7 | 10.6 | 41.3 | — |
| Compound 34 | 12.1 | 31.6 | 81.3 |

TABLE 7-continued

| | Hyaluronic acid-degrading enzyme activity inhibition ratio (%) | | |
|---|---|---|---|
| | 0.1 mg/mL | 0.2 mg/mL | 0.4 mg/mL |
| Magnesium ascorbate phosphate | 3.3 | 4.2 | 7.6 |

As a result, it was found that the compounds of the invention each had an inhibitory effect of hyaluronic acid-degrading enzyme activity.

Test Example 8

Using the compound 7 obtained in Example 2 as well as dl-α-tocopherol (manufactured by Tokyo Kasei Kogyo Co., Ltd.) and butylhydroxytoluene (BHT) as comparative controls, a test of scavenging DDPH (1,1-diphenyl-2-picrylhydrazyl) radical, a stable radical, was carried out.

Specific Test Procedure is as Follows.

1 ml of 200 µM DPPH ethanol solution was added to 800 µl of 100 mM Tris-HCl buffer (pH 7.4) and 200 µl of an ethanol solution of the compound 7 (a final concentration of 10 µg/mL), followed by sufficient stirring. After the resulting mixture was allowed to stand in a dark place at room temperature for 20 minutes, the absorbance at 517 nm was measured (absorbance of the test solution)

The compound 13 of the invention as well as dl-α-tocopherol and butylhydroxytoluene as a known radical scavenger were similarly tested.

As a control, 800 µl of 100 mM Tris-HCl buffer (pH 7.4), 200 µl of ethanol, and 1 ml of 200 µM DPPH ethanol solution were used in the same manner as described above and the absorbance was measured (absorbance of the control solution).

With the individual compounds, the same measurement was repeated three times, and the mean value was inserted in the following formula to calculate a DPPH radical-scavenging ratio (%). The results are shown in Table 8.

DPPH radical-scavenging ratio (%)=[1−(absorbance of sample solution/absorbance of control solution)]×100

TABLE 8

| | DPPH radical-scavenging ratio (%) |
|---|---|
| Compound 7 | 33.7 |
| Compound 13 | 39.0 |
| Tocopherol | 28.4 |
| BHT | 63.7 |

It was found that, although inferior to BHT, the compounds of the invention each had a radical-scavenging activity equal to or higher than that of dl-α-tocopherol. Therefore, it is judged that the compounds of the invention can be used as scavengers of active oxygen, particularly hydroxy radicals.

Test Example 9

Using the compound 36 obtained in Example 20, the compound 37 obtained in Example 21, the compound 38 obtained in Example 22, the compound 39 obtained in Example 23, the compound 40 obtained in Example 24, the compound 42 obtained in Example 26, the compound 45 obtained in Example 29, the compound 46 obtained in Example 30, the compound 48 obtained in Example 32 and, as a comparative control, dl-α-tocopherol (manufactured by Tokyo Kasei Kogyo Co., Ltd.), a test of scavenging DDPH (1,1-diphenyl-2-picrylhydrazyl) radical, a stable radical, was carried out.

Specific Test Procedure is as Follows.

100 µl of 800 µM DPPH ethanol solution was added to 80 µl of 100 mM Tris-HCl buffer (pH 7.4) and 20 µl of an ethanol solution of the compound 36 (final concentration of 25 µg/mL), followed by sufficient stirring. After the resulting mixture was allowed to stand in a dark place at room temperature for 20 minutes, the absorbance at 540 nm was measured on a microplate reader (absorbance of the test solution).

The compounds 37, 38, 39, 40, 42, 45, 46, and 48 of the invention as well as dl-α-tocopherol as a known radical scavenger were similarly tested.

As a control, using 80 µl of 100 mM Tris-HCl buffer (pH 7.4), 20 µl of ethanol, and 100 µl of 800 µM DPPH ethanol solution, the same operation was carried out as described above and the absorbance was measured (absorbance of the control solution).

With the individual compounds, the same measurement was repeated four times, and the mean value was inserted in the following formula to calculate a DPPH radical-scavenging ratio. The results are shown in Table 9.

DPPH radical-scavenging ratio (%)=[1−(absorbance of sample solution/absorbance of control solution)]×100

TABLE 9

| | DPPH radical-scavenging ratio (%) |
|---|---|
| Compound 36 | 31.7 |
| Compound 37 | 37.6 |
| Compound 38 | 32.5 |
| Compound 39 | 33.8 |
| Compound 40 | 33.9 |
| Compound 42 | 40.7 |
| Compound 45 | 38.4 |
| Compound 46 | 39.4 |
| Compound 48 | 33.5 |
| Tocopherol | 14.9 |

It was found that the compounds of the invention each had a radical-scavenging activity higher than that of dl-α-tocopherol. Therefore, it is judged that the compounds of the invention can be used as scavengers of active oxygen, particularly hydroxy radicals.

Test Example 10

Using the compound 7 obtained in Example 2, the compound 38 obtained in Example 22, the compound 40 obtained in Example 24, the compound 42 obtained in Example 26, the compound 46 obtained in Example 30, and as a comparative control, dl-α-tocopherol (manufactured by Tokyo Kasei Kogyo Co., Ltd.), a test of suppressing lipid peroxide formation was carried out using linoleic acid.

Specific Test Procedure is as Follows.

(1) After ethanol (2.0 g) was added to linoleic acid (0.2 g, manufactured by Tokyo Kasei Kogyo Co., Ltd.), the compound 7 (0.01 g), and a surfactant Nissan OT-221 (0.4 g, manufactured by NOF Corporation) placed in a 50-ml screw vial and they was dissolved one another, distilled water (17.39 g) was added to the resulting solution and the whole was stirred. Then, the whole was tightly sealed and allowed to stand in a constant-temperature chamber at 40° C. Such sample was prepared in a duplex manner.

The same operation was carried out on the compounds 38, 40, 42, 46, dl-α-tocopherol, and a sample with addition of no test compound (blank).

(2) The amount of remaining linoleic acid after one week, 2 weeks, 3 weeks, and 4 weeks from the start of the test was quantitatively determined by HPLC.

The HPLC analytical conditions were as follows: Wavelength for detection: 210 nm; Mobile phase: a mixed solution of a Mc Ilvaine buffer adjusted to pH 2.6 and methanol (10:90); Flow rate: 1 ml/min; Column: ODS-80Ts (4.6 φmm×150 mm); and Column temperature: 40° C.

(3) Quantitative determination by HPLC was carried out on each sample one time. The ratio of remaining linoleic acid was calculated on the basis of the mean value of values obtained in two-times measurement. The results are shown in Table 10.

TABLE 10

| | Ratio of remaining linoleic acid (%) | | | |
|---|---|---|---|---|
| | After 1 week | After 2 weeks | After 3 weeks | After 4 weeks |
| Blank | 81.3 | 60.6 | 40.6 | 19.1 |
| Compound 7 | 99.3 | 95.1 | 82.0 | 63.4 |
| Compound 38 | 99.7 | 95.5 | 83.9 | 74.8 |
| Compound 40 | 99.9 | 97.5 | 86.2 | 75.5 |
| Compound 42 | 99.3 | 95.4 | 83.3 | 74.1 |
| Compound 46 | 98.8 | 94.6 | 90.5 | 74.0 |
| Tocopherol | 88.7 | 81.3 | 69.7 | 50.0 |

As a result of the test, it was found that the compounds 7, 38, 40, 42, and 46 of the invention each had an effect higher than that of dl-α-tocopherol, an existing lipid peroxide formation-suppressing agent.

INDUSTRIAL APPLICABILITY

The compounds of the present invention can be industrially produced and they exhibit characteristics such as excellent tyrosinase activity inhibitory effect, hyaluronic acid-degrading enzyme activity inhibitory effect, hydroxy radical-scavenging action, and lipid peroxide formation-suppressing action. Accordingly, it is possible for the compounds of the invention to apply to the fields of foods, medicines, quasi-drugs, cosmetics, etc. As specific examples, the compounds can be used in applications for preventing spots, freckles, aging of skin, allergy, and the like.

The invention claimed is:

1. A compound represented by the following formula (1):

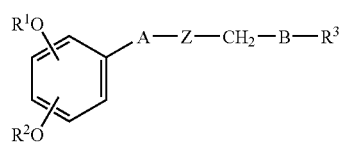

(1)

(wherein $R^1$ is a hydrogen atom, a lower alkyl group, or a protective group of a phenolic hydroxyl group, $R^2$ is a hydrogen atom or a protective group of a phenolic hydroxyl group, A is an alkylene group having 1 to 4 carbon atoms, B is an alkylene group having 1 to 12 carbon atoms, $R^3$ is —COOR$^4$ (wherein $R^4$ is a protective group of a carboxyl group), a carboxyl group, or —CH$_2$OH, and Z is —CO—CH═CH—, —CHOH—CH═CH—, —CHOH—1,2-epoxy-, —CHOH—CH$_2$CH$_2$—, —CHOH—CH$_2$CHOH—, —CO—CH$^2$CHOR$^5$—, —CHOH—CH$_2$CHOR$^5$—, a ketal derivative of —CO—CH═CH—, or a ketal derivative of —CO—CH$_2$CH$_2$— and $R^5$ is a lower alkyl group when $R^3$ is a —COOR$^4$ group, Z is —CO—CH═CH—, —CHOH—CH═CH—, —CHOH—1,2-epoxy-, —CHOH—CH$_2$CH$_2$—, —CHOH—CH$_2$CHOH—, —CO—CH$^2$CHOR$^5$—, —CHOH—CH$_2$CHOR$^5$—, a ketal derivative of —CO—CH═CH—, or a ketal derivative of —CO—CH$_2$CH$_2$— and $R^5$ is a lower alkyl group when $R^3$ is a carboxyl group, or Z is —CHOH—CH═CH—, —CHOH—1,2-epoxy-, —CHOH—CH$^2$CHOH—, —CO—CH$_2$CHOR$^5$—, —CHOH—CH$_2$CHOR$^5$—, a ketal derivative of —CO—CH═CH—, or a ketal derivative of —CO—CH$_2$CH$_2$— and $R^5$ is a lower alkyl group when $R^3$ is a —CH$_2$OH).

2. A tyrosinase inhibitor composition comprising the compound represented by the formula (1) according to claim 1.

3. A hyaluronic acid-degrading enzyme inhibitor composition comprising the compound represented by the formula (1) according to claim 1.

4. An antioxidant composition comprising the compound represented by the formula (1) according to claim 1.

5. A tyrosinase inhibitor composition containing a compound represented by the following formula (2):

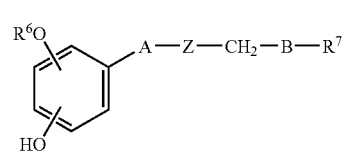

(2)

(wherein $R^6$ is a hydrogen atom, a lower alkyl group, or a protective group of a phenolic hydroxyl group, A is an alkylene group having 1 to 4 carbon atoms, B is an alkylene group having 1 to 12 carbon atoms, $R^7$ is —COOR$^8$ (wherein $R^8$ is a protective group of a carboxyl group), a carboxyl group, or —CH$_2$OH, Z is —CO—CH═CH—, —CHOH—CH═CH—, —CHOH—1,2-epoxy-, —CHOH—CH$_2$CH$_2$—, —CHOH—CH$_2$CHOH—, —CO—CH$_2$CHOR$^9$—, —CHOH—CH$_2$CHOR$^9$—, a ketal derivative of —CO—CH═CH—, or a ketal derivative of —CO—CH$_2$CH$_2$—, and $R^9$ is a lower alkyl group).

6. A hyaluronic acid-degrading enzyme inhibitor composition comprising the compound represented by the above formula (2).

7. An antioxidant composition comprising the compound represented by the above formula (2).

* * * * *